United States Patent [19]

Ziemer et al.

[11] Patent Number: 5,972,839
[45] Date of Patent: Oct. 26, 1999

[54] 2-FLUOROACRYLIC ACID DERIVATIVES, NOVEL MIXTURES OF HERBICIDES AND ANTIDOTES, AND THEIR USE

[75] Inventors: Frank Ziemer, Kriftel; Lothar Willms, Hofheim; Klaus Bauer, Hanau; Hermann Bieringer, Eppstein; Christopher Rosinger, Hofheim, all of Germany; Jacques Demassey, Chalifert, France

[73] Assignee: Hoechst Schering AgrEvo GmbH, Berlin, Germany

[21] Appl. No.: 08/991,960

[22] Filed: Dec. 17, 1997

[30] Foreign Application Priority Data

Dec. 19, 1996 [DE] Germany ............... 196 52 961

[51] Int. Cl.$^6$ ............... A01N 43/40; A01N 31/02; C07D 213/26; C07C 69/653
[52] U.S. Cl. ............... 504/223; 504/314; 504/321; 546/341; 560/104; 562/495
[58] Field of Search ............... 546/341; 504/223, 504/314, 321; 560/104; 562/495

[56] References Cited

U.S. PATENT DOCUMENTS

| | | | |
|---|---|---|---|
| 4,347,372 | 8/1982 | Fory et al. | 514/352 |
| 5,380,733 | 1/1995 | Cockerill et al. | 514/352 |

FOREIGN PATENT DOCUMENTS

| | | |
|---|---|---|
| 0012158 | 6/1980 | European Pat. Off. . |
| 0547972 | 6/1993 | European Pat. Off. . |
| 1542872 | 7/1970 | Germany . |
| 7102436 | 2/1971 | Netherlands . |
| 1301371 | 12/1972 | United Kingdom . |
| WO 91/16301 | 10/1991 | WIPO . |

OTHER PUBLICATIONS

J. Am. Chem. Soc. (1993), 115 (16), 7103–10, XP002064658.
Journal of Fluorine Chemistry, vol. 48, No. 2, 1990, pp. 281–292.
Synthesis, No. 2, 1975, pp. 122–125.
Chemical Abstracts, Columbus, Ohio, vol. 124, No. 5, 1996, Abstract No. 55063.
Bergmann et al., J. Chem. Soc., 1961, 4033–4038.
Robinson et al., Tetrahedron 46(2), 335–340, 1990.

*Primary Examiner*—Zinna Northington Davis
*Attorney, Agent, or Firm*—Frommer Lawrence & Haug LLLP

[57] ABSTRACT

The invention relates to novel α-fluoroacrylic acid derivatives, to active compound/antidote combinations which comprise α-fluoroacrylic acid derivatives and are outstandingly suitable for use in crops of useful plants, to their use and to methods for protecting crop plants.

10 Claims, No Drawings

2-FLUOROACRYLIC ACID DERIVATIVES, NOVEL MIXTURES OF HERBICIDES AND ANTIDOTES, AND THEIR USE

The invention relates to the technical field of crop protection agents, in particular α-fluoroacrylic acid derivatives and active compound/antidote combinations which are outstandingly suitable for use against competing harmful plants in crops of useful plants.

When using agents for treating plants, and in particular when using herbicides, undesirable damage can occur in the treated crop plants. In particular when the herbicides are not fully compatible with (not selective in) important crop plants, their use is considerably restricted. In some cases, they can therefore not be employed at all or only at application rates so low that the desired broad herbicidal activity is not ensured. For example, many herbicides from the group of the sulfonylureas can not be employed selectively in maize. It is desirable to reduce this phytotoxicity, in particular when applying herbicides by the post-emergence method.

α-Chlorocinnamic acid derivatives as herbicides are disclosed in DE OS 1 542 872. Moreover, processes for preparing arylalkanecarboxylic acids as plant growth regulators are described in NL 7 102 436.

α-Fluorocinnamic acid derivatives and α-fluoropyridylacrylic acid derivatives have already been described by Bergmann and Shahak in J. Chem. Soc., 1961, 4033–4038. Further 3- or 4-substituted α-fluorocinnamic acid derivatives have been described by Robinson and Stablein, (1990), Tetrahedron 46(2), 335–340.

Quite unexpectedly, new experiments have shown that α-fluoroacrylic acid derivatives are outstandingly suitable for reducing the phytotoxic side effects of herbicides in crop plants significantly or for totally eliminating them.

The present invention therefore provides herbicide/safener combinations which comprise A) at least one herbicidally active compound and
B) at least one 2-fluoroacrylic acid derivative of the formula (I)

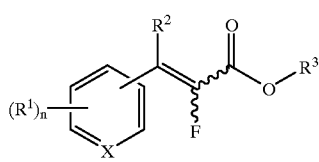

(I)

in which

X is CH or N;

n, in the case that X=N, is an integer from 0 to 4 and, in the case that X=CH, is an integer from 0 to 5;

$R^1$ is halogen, $(C_1-C_8)$-alkyl, $(C_2-C_8)$-alkenyl, $(C_2-C_8)$-alkynyl, $(C_3-C_6)$-cycloalkyl, $(C_5-C_6)$-cycloalkenyl, aryl, $(C_1-C_8)$-alkoxy, $(C_2-C_8)$-alkenyloxy, $(C_2-C_8)$-alkynyloxy, phenoxy, sulfamoyl, amino, mono- or di-$(C_1-C_4)$-alkylamino, nitro, hydroxyl, mono- or di-$(C_1-C_4)$-alkylaminosulfonyl, cyano, $(C_1-C_8)$-alkylthio, $(C_1-C_8)$-alkylsulfinyl, $(C_1-C_8)$-alkylsulfonyl, $(C_1-C_8)$-alkoxycarbonyl, $(C_1-C_8)$-alkylthiocarbonyl or $(C_1-C_8)$-alkylcarbonyl, where each of the above-mentioned carbon-containing radicals is unsubstituted or substituted by one or more, preferably up to three, identical or different radicals selected from the group consisting of halogen, halo-$(C_1-C_8)$-alkoxy, phosphoryl, nitro, amino, mono- or di-$(C_1-C_4)$-alkylamino, cyano, hydroxyl and $(C_1-C_8)$-alkoxy where one or more, preferably up to three, $CH_2$ groups may be replaced by oxygen and, in the case of cyclic radicals, substituted by one or more, preferably up to three, identical or different radicals selected from the group consisting of halogen, halo-$(C_1-C_8)$-alkoxy, phosphoryl, nitro, amino, mono- or di-$(C_1-C_4)$-alkylamino, cyano, hydroxyl, $(C_1-C_8)$-alkoxy, $(C_1-C_4)$-alkyl and $(C_1-C_4)$-haloalkyl, or two of the radicals $R^1$ together, in the case that n is an integer greater than 1, may also be unsubstituted or substituted 1,ω-dioxoalkylene;

$R^2$ is hydrogen, $(C_1-C_6)$-alkyl, $(C_2-C_6)$-alkenyl, $(C_3-C_6)$-cycloalkyl, $(C_5-C_6)$-cycloalkenyl or substituted aryl;

$R^3$ is hydrogen, $(C_1-C_{18})$-alkyl, $(C_3-C_{12})$-cycloalkyl, $(C_2-C_{18})$-alkenyl, $(C_5-C_6)$-cycloalkenyl, $(C_2-C_{18})$-alkynyl, aryl or $-N=CR^4R^5$, where each of the abovementioned carbon-containing radicals is unsubstituted or substituted by one or more, preferably up to three, identical or different radicals selected from the group consisting of halogen, nitro, cyano, hydroxyl, $(C_1-C_8)$-alkoxy where one or more, preferably up to three, $CH_2$ groups may be replaced by oxygen, $(C_1-C_8)$-alkylthio, $(C_1-C_6)$-alkylsulfinyl, $(C_1-C_6)$-alkylsulfonyl, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, mono- or di-$(C_1-C_4)$-alkylamino, $(C_1-C_8)$-alkoxycarbonyl, $(C_2-C_8)$-alkenyloxycarbonyl, $(C_2-C_8)$-alkynyloxycarbonyl, $(C_1-C_8)$-alkylthiocarbonyl, $(C_1-C_8)$-alkylcarbonyl, $(C_2-C_8)$-alkenylcarbonyl, $(C_2-C_8)$-alkynylcarbonyl, $(C_1-C_8)$-alkylcarbonylamino, $(C_2-C_8)$-alkenylcarbonylamino, $(C_2-C_8)$-alkynylcarbonylamino, $(C_1-C_8)$-alkylcarbonyloxy, $(C_1-C_8)$-alkylcarbamoyl, phenyl, phenyl-$(C_1-C_4)$-alkoxy, phenoxy, phenoxy-$(C_1-C_4)$-alkoxy and phenoxycarbonyl, where the last 28 radicals are unsubstituted or substituted by one or more, preferably up to three, identical or different radicals selected from the group consisting of halogen, halo-$(C_1-C_8)$-alkoxy, nitro, amino, mono- or di-$(C_1-C_4)$-alkylamino, cyano, hydroxyl and $(C_1-C_8)$-alkoxy where one or more, preferably up to three, $CH_2$ groups may be replaced by oxygen and, in the case of cyclic radicals, substituted by one or more identical or different radicals selected from the group consisting of halogen, nitro, amino, mono- or di-$(C_1-C_4)$-alkylamino, cyano, hydroxyl, $(C_1-C_4)$-alkyl and $(C_1-C_4)$-haloalkyl and $R^4$ and $R^5$ independently of one another are each hydrogen or $(C_1-C_6)$-alkyl;

or salts thereof.

Preference is given to those herbicide/safener combinations which comprise, as component A) at least one herbicidally active compound selected from the group consisting of phenoxyphenoxycarboxylic esters, heteroaryloxyphenoxycarboxylic esters, sulfonylureas, cyclohexanediones, benzoylcyclohexanediones, imidazolinones, triazolopyrimidinesulfonamides, pyrimidinyloxypyrimidinecarboxylic acid derivatives, pyrimidinyloxybenzoic acid derivatives and S-(N-aryl-N-alkylcarbamoylmethyl)dithiophosphonic esters.

Preference is also given to those herbicide/safener combinations which comprise, as component B) at least one compound of the formula (I) in which
X is CH;
n is an integer from 0 to 3;
$R^1$ is halogen, $(C_1-C_4)$-alkyl, $(C_2-C_4)$-alkenyl, $(C_3-C_6)$-cycloalkyl, aryl, $(C_1-C_4)$-alkoxy, $(C_2-C_4)$-alkenyloxy, $(C_2-C_4)$-alkynyloxy, phenoxy, amino, mono- or di-$(C_1-C_4)$-alkylamino, nitro, hydroxyl, mono- or di-$(C_1-C_4)$-alkylaminosulfonyl, cyano, $(C_1-C_4)$-alkylthio, $(C_1-C_4)$-alkylsulfinyl, $(C_1-C_4)$-alkylsulfonyl, $(C_1-C_4)$-alkoxycarbonyl, $(C_1-C_4)$-alkylthiocarbonyl or $(C_1-C_4)$-alkylcarbonyl, where each of the abovementioned carbon-containing radicals is unsubstituted or substituted by one or more, preferably up to three, identical or different radicals selected from the group consisting of halogen, halo-$(C_1-C_8)$-alkoxy, nitro, amino, mono- or di-$(C_1-C_4)$-alkylamino, cyano, hydroxyl and $(C_1-C_8)$-alkoxy where one or more $CH_2$ groups may be replaced by oxygen, and may also be substituted, in the case of cyclic radicals, by $(C_1-C_4)$-alkyl and $(C_1-C_4)$-haloalkyl, or two of the radicals $R^1$ together, in the case that n is an integer greater than 1, are also an unsubstituted or substituted 1,ω-dioxoalkylene;
$R^2$ is hydrogen or $(C_1-C_4)$-alkyl and
$R^3$ is hydrogen, $(C_1-C_8)$-alkyl, $(C_3-C_6)$-cycloalkyl, $(C_2-C_6)$-alkenyl, $(C_2-C_6)$-alkynyl or aryl, where each of the abovementioned carbon-containing radicals is unsubstituted or substituted by one or more, preferably up to three, identical or different radicals selected from the group consisting of halogen, nitro, cyano, hydroxyl, $(C_1-C_8)$-alkoxy where one or more, preferably up to three, $CH_2$ groups may be replaced by oxygen, $(C_1-C_8)$-alkylthio, $(C_1-C_6)$-alkylsulfinyl, $(C_1-C_6)$-alkylsulfonyl, $(C_2-C_4)$-alkenyloxy, $(C_2-C_4)$-alkynyloxy, $(C_3-C_6)$-cycloalkyl, mono- or di-$(C_1-C_4)$-alkylamino, $(C_1-C_8)$-alkoxycarbonyl, $(C_1-C_4)$-alkylcarbonyl, $(C_2-C_4)$-alkenylcarbonyl, $(C_1-C_4)$-alkylcarbonyloxy, phenyl, phenyl-$(C_1-C_4)$-alkoxy, phenoxy and phenoxy-$(C_1-C_4)$-alkoxy, where the last 16 radicals are unsubstituted or substituted by one or more, preferably up to three, identical or different radicals selected from the group consisting of halogen, nitro, amino, mono- or di-$(C_1-C_4)$-alkylamino, cyano and hydroxyl and, in the case of cyclic radicals, also of $(C_1-C_4)$-alkyl and $(C_1-C_4)$-haloalkyl,
or salts thereof.

Particular preference is given to herbicide/safener combinations which comprise, as component
B) at least one compound of the formula (I) in which
X is CH or N;
n, in the case that X=N, is an integer from 0 to 4, and in the case that X=CH, is an integer from 0 to 5;
$R^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl or phenyl or phenoxy, where the last two radicals are unsubstituted or substituted by one or more, preferably up to three, identical or different radicals selected from the group consisting of halogen, $(C_1-C_4)$-alkyl, $(C_1-C_4)$-haloalkyl, $(C_1-C_8)$-alkoxy, halo-$(C_1-C_8)$-alkoxy, nitro, amino, mono- or di-$(C_1-C_4)$-alkylamino and cyano, or two of the radicals $R^1$ together, in the case that n is an integer greater than 1, are also an unsubstituted or substituted 1,ω-dioxoalkylene;
$R^2$ is hydrogen or $(C_1-C_4)$-alkyl and
$R^3$ is hydrogen, $(C_1-C_8)$-alkyl, $(C_2-C_4)$-alkenyl or $(C_2-C_4)$-alkynyl, where each of the abovementioned carbon-containing radicals is unsubstituted or substituted by one or more, preferably up to three, identical or different radicals selected from the group consisting of halogen and $(C_1-C_4)$-alkoxy,
or salts thereof.

In formula (I) and in all formulae hereinbelow, the radicals alkyl, alkoxy, haloalkyl, haloalkoxy, alkylamino and alkylthio and the corresponding unsaturated and/or substituted radicals can in each case be straight-chain or branched in the carbon skeleton.

Alkyl radicals, also in the composite meanings such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals have the meanings of the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is for example, propargyl, but-2-yn-1-yl, but-3-yn-1-yl, 1-methylbut-3-yn-1-yl.

Cycloalkyl is a carbocyclic saturated ring system, for example cyclopropyl, cyclobutyl, cyclopentyl or cyclohexyl.

Substituted cycloalkyl is a carbocyclic saturated ring system defined under "cycloalkyl" which is substituted for example by one or more identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy, amino, mono- or di-$(C_1-C_4)$-alkylamino, nitro, cyano, alkoxycarbonyl and alkylcarbonyl.

Halogen is fluorine, chlorine, bromine or iodine, preferably fluorine or chlorine; haloalkyl, haloalkenyl and haloalkynyl is alkyl, alkenyl and alkynyl, respectively, which is partially or fully substituted by halogen, preferably by fluorine, chlorine and/or bromine, in particular by fluorine or chlorine, such as monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $OCF_2CF_3$, $OCH_2CF_3$ and $OCH_2CH_2Cl$; the same applies analogously to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and similar radicals, preferably phenyl.

Substituted aryl, aryloxy, heteroaryl, heteroaryloxy, phenoxy, benzyl, benzyloxy or substituted bicyclic radicals having aromatic moieties are, for example, a substituted radical derived from the unsubstituted skeleton, the substituents being, for example, one or more, preferably up to 3, radicals selected from the group consisting of halogen, alkyl, haloalkyl, alkoxy, haloalkoxy, hydroxyl, amino, nitro, cyano, alkoxycarbonyl, alkylcarbonyl, formyl, carbamoyl, monoalkylaminocarbonyl, dialkylaminocarbonyl, monoalkylamino, dialkylamino, alkylsulfinyl and alkylsulfonyl, the radicals having up to 4 carbon atoms, in particular 1 or 2 carbon atoms, being preferred for radicals containing carbon atoms. Preference is generally given to substituents selected from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano.

Substituted phenyl is, for example, phenyl which is mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example, o-, m- and p-tolyl, dimethylphenyls, 2-, 3- and 4-chlorophenyl, 2-, 3- and 4-trifluoro- and trichlorophenyl, 2,4-, 3,5-, 2,5- and 2,3-dichlorophenyl, o-, m- and p-methoxyphenyl.

Substituted dioxoalkylene is, for example, a dioxoalkylene radical which is mono- or polysubstituted by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, preferably a 1,ω-dioxoalkylene radical.

The compounds of the formula (I) contain one or more asymmetric carbon atoms or else double bonds which are not specifically indicated in the formula (I). The stereoisomers which are possible and which are defined by their specific spatial form, such as enantiomers, diastereomers, Z and E isomers, are all embraced by the formula (I) and can be obtained by customary methods from mixtures of the stereoisomers, or else be prepared by stereoselective reactions in combination with the use of stereochemically pure starting materials.

The present invention provides the compounds of the formula (I) in form of the free base or of a salt, preferably an acid addition salt. Acids which can be employed for salt formation include inorganic acids such as hydrochloric acid, hydrobromic acid, nitric acid, sulfuric acid, phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid. Further particularly preferred salts are possible when the compounds contain acidic groups such as carboxyl or phenolic hydroxyl where one hydrogen is replaced by an agriculturally suitable cation. Salts of compounds of the formula (I) are, for example, metal salts, in particular alkali metal salts or alkaline earth metal salts, in particular sodium, potassium and ammonium salts or salts with organic amines such as, for example, $(C_1-C_4)$-alkylamines or $(C_1-C_4)$-hydroxyalkylamines. Furthermore, acid addition salts can be formed by reaction of basic groups, such as amino groups with or without substitution or basic heterocycles, with inorganic or organic acids.

The invention also provides a method for protecting crop plants, preferably crops of cereals (wheat, rye, barley, oats, rice, maize, sorghum), but also cotton and soybean, in particular cereals, particularly preferably maize plants, against phytotoxic side effects of herbicides, in particular sulfonylurea herbicides, which comprises applying an effective amount of at least one compound of the formula (I) before, after or together with the abovementioned herbicidally active compound to the plants, seeds of plants or the area under cultivation.

The invention furthermore provides the use of compounds of the formula (I) for protecting crop plants, preferably cereals or maize plants, against phytotoxic side effects of herbicides, in particular sulfonylurea herbicides.

Furthermore, the invention provides novel 2-fluoroacrylic acid derivatives of the formula (I)

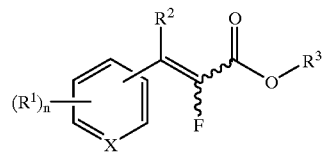

in which

X, n, $R^1$, $R^2$ and $R^3$ are each as defined above or salts thereof, except for the compounds below:
a) α-fluorocinnamic acid or the methyl or ethyl ester thereof,
b) ethyl 3- or 4-methyl-α-fluorocinnamate,
c) 3- or 4-chloro-α-fluorocinnamic acid or the methyl or ethyl ester thereof,
d) ethyl 2-hydroxy-α-fluorocinnamic acid,
e) ethyl α-fluoro-β-2-pyridylacrylate,
f) ethyl α-fluoro-β-3-pyridylacrylate,
g) ethyl 3- or 4-methoxy-α-fluorocinnamate,
h) ethyl 3- or 4-phenoxy-α-fluorocinnamate,
j) ethyl 4-phenyl-α-fluorocinnamate,
k) 3- or 4-fluoro-α-fluorocinnamic acid or the methyl or ethyl ester thereof,
l) 3- or 4-bromo-α-fluorocinnamic acid or the ethyl ester thereof,
m) ethyl 4-carboxyethyl-α-fluorocinnamate,
n) methyl or ethyl 3- or 4-trifluoromethyl-α-fluorocinnamate,
o) ethyl 3- or 4-cyano-α-fluorocinnamate,
p) ethyl 3- or 4-nitro-α-fluorocinnamate.

The compounds of the formula (I) can be prepared by generally known methods [Robinson et al., Tetrahedron 46 (1990) 335–340; Bergman et al., J. Chem. Soc., (1961), 4033–4038; Ishihara et al., Chem. Lett., (1987), 1145–1148; U.S. Pat. No. 4,338,253; Piva, Synlett, (1994), 729–731; Bergmann et al., J. Chem. Soc., (1968), 1232–1235].

Moreover, the invention provides a process for preparing 2-fluoroacrylic acid derivatives of the formula (I), which comprises reacting an aldehyde or ketone of the formula (II)

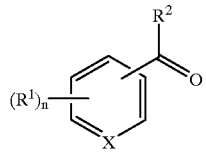

in which

X, $R^1$, $R^2$ and n are each as defined in formula (I)
a) with diethyloxalofluoroacetate or
b) with triethyl 2-fluoro-2-phosphonoacetate to give the ethyl ester which is, if $R^3$ is not ethyl, subsequently reacted by customary methods to give the compound of the formula (I).

The compounds of the formula $(I_Z)$, which are predominantly of Z configuration, can be prepared for example according to the scheme below by reacting an aldehyde or a ketone of the formula (II)

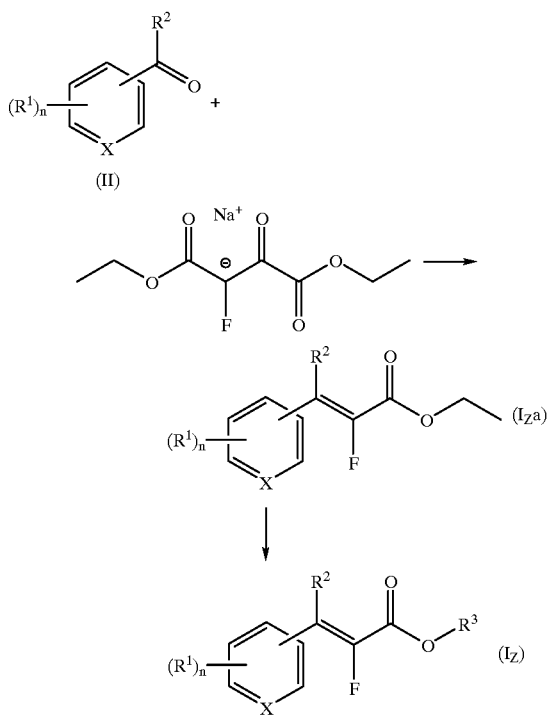

in which

X, R¹, R² and n are each as defined in formula (I) with the sodium salt of diethyl oxalofluoroacetate, which is accessible from ethyl fluoroacetate and diethyl oxalate using sodium hydride, to give initially the ethyl ester ($I_Z$a) which is subsequently transesterified by customary methods (variant 1).

The compounds of the formula ($I_E$) which are of E configuration, are accessible for example according to the following scheme by reacting an aldehyde or a ketone of the formula (II)

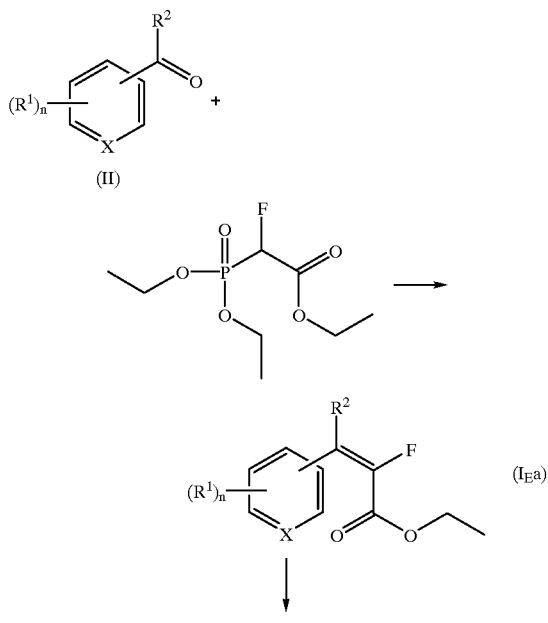

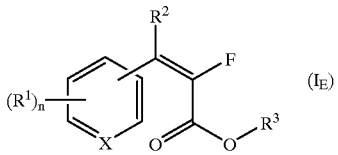

in which

X, R¹, R² and n are each as defined in formula (I) with triethyl 2-fluoro-2-phosphonoacetate in the presence of butyllithium to give initially the ethyl ester ($I_E$a) which is subsequently transesterified by customary methods (variant 2).

The reactions of variant 1 are preferably carried out in an inert organic solvent or solvent mixture. Suitable solvents are, for example, tetrahydrofuran (THF), dioxane, acetonitrile or dimethylformamide.

The reaction temperatures are preferably in the range between −20° C. and 100° C.

The reactions of variant 2 are likewise preferably carried out in an inert organic solvent or solvent mixture in the presence of at least one strong base such as, for example, butyllithium. A suitable solvent is, for example, THF.

The reaction temperatures are preferably in the range between −100° C. and 20° C.

If the safeners of the formula (I) according to the invention are applied in subtoxic concentrations together with the herbicidally active compounds, or else in any order, they are capable of reusing or completely reversing the phytotoxic side effects of these herbicides without reducing the efficacy of the herbicides against harmful plants.

Suitable herbicides which can be combined with the safeners according to the invention are, for example:

A) herbicides of the type of the phenoxyphenoxy- and heteroaryloxyphenoxycarboxylic ($C_1$–$C_4$)-alkyl esters, ($C_2$–$C_4$)-alkenyl esters and ($C_3$–$C_4$)-alkynyl esters such as A1) phenoxyphenoxy- and benzyloxyphenoxycarboxylic acid derivatives, for example methyl 2-(4-(2,4-dichlorophenoxy)phenoxy)propionate (diclofopmethyl), methyl 2-(4-(4-bromo-2-chlorophenoxy)phenoxy) propionate (see DE-A-2601548), methyl 2-(4-(4-bromo-2-fluorophenoxy)phenoxy) propionate (see U.S. Pat. No. 4,808,750), methyl 2-(4-(2-chloro-4-trifluoromethylphenoxy)phenoxy) propionate (see DE-A-2433067), methyl 2-(4-(2-fluoro-4-trifluoromethylphenoxy)phenoxy) propionate (see U.S. Pat. No. 4,808,750), methyl 2-(4-(2,4-dichlorobenzyl)phenoxy)propionate (see DE-A-2417487), ethyl 4-(4-(4-methylphenoxy)phenoxy)pent-2-enoate, methyl 2-(4-(4-trifluoromethylphenoxy)phenoxy) propionate (see DE-A-2433067), A2) "mononuclear" heteroaryloxyphenoxyalkanecarboxylic acid derivatives, for example ethyl 2-(4-(3,5-dichloropyridyl-2-oxy)phenoxy)propionate (see EP-A-2925), propargyl 2-(4-(3,5-dichloropyridyl-2-oxy)phenoxy) propionate (EP-A-3114), methyl 2-(4-(3-chloro-5-trifluoromethyl-2-pyridyloxy) phenoxypropionate (see EP-A-3890), ethyl 2-(4-(3-chloro-5-trifluoromethyl-2-pyridyloxy) phenoxy)propionate (see EP-A-3890), propargyl 2-(4-(5-chloro-3-fluoro-2-pyridyloxy)phenoxy) propionate (EP-A-191736), butyl 2-(4-(5-trifluoromethyl-2-pyridyloxy)phenoxy) propionate(fluazifop-butyl), A3) "binuclear" heteroaryloxyphenoxyalkanecarboxylic acid derivatives, for example
methyl and ethyl 2-(4-(6-chloro-2-quinoxalyloxy)phenoxy) propionate(quizalofop-methyl and -ethyl),
methyl 2-(4-(6-fluoro-2-quinoxalyloxy)phenoxy)propionate (see J. Pest. Sci. Vol. 10, 61 (1985)),
2-(4-(6-chloro-2-quinoxalyloxy)phenoxy)propionic acid and 2-isopropylidenea-minooxyethyl 2-(4-(6-chloro-2-quinoxalyloxy)-phenoxy)propionate(propaquizafop and ester),
ethyl 2-(4-(6-chlorobenzoxazol-2-yloxy)phenoxy) propionate(fenoxaprop-ethyl), its D(+) isomer (fenoxaprop-P-ethyl) and
ethyl 2-(4-(6-chlorobenzothiazol-2-yloxy) phenoxypropionate (see DE-A-2640730),
tetrahydrofur-2-ylmethyl 2-(4-(6-chloroquinoxalyloxy) phenoxypropionate (see EP-A 323 727).

B) Herbicides from the sulfonylurea series such as, for example, pyrimidinyl- or triazinylaminocarbonyl[benzene-, pyridine-, pyrazole-, thiophene- and (alkylsulfonyl) alkylamino]sulfamides. Preferred as substituents on the pyrimidine ring or triazine ring are alkoxy, alkyl, haloalkoxy, haloalkyl, halogen or dimethylamino, it being possible for all substituents to be combined independently of one another. Preferred substituents in the benzene-, pyridine-, pyrazole-, thiophene- or (alkylsulfonyl) alkylamino moiety are alkyl, alkoxy, halogen, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkansulfonyl) alkylamino.

Examples of suitable sulfonylureas are

B1) phenyl- and benzylsulfonylureas and related compounds, for example
1-(2-chlorophenylsulfonyl)-3-(4-methoxy-6-methyl-1,3,5-triazin-2-yl)urea(chlorsulfuron),
1-(2-ethoxycarbonylphenylsulfonyl)-3-(4-chloro-6-methoxypyrimidin-2-yl)urea(chlorimuron-ethyl),
1-(2-methoxyphenylsulfonyl)-3-(4-methoxy-6-methyl-1,3,5-triazin-2-yl)urea(metsulfuron-methyl),
1-(2-chloroethoxyphenylsulfonyl)-3-(4-methoxy-6-methyl-1,3,5-triazin-2-yl)urea(triasulfuron),
1-(2-methoxycarbonylphenylsulfonyl)-3-(4,6-dimethylpyrimidin-2-yl)urea(sulfometuron-methyl),
1-(2-methoxycarbonylphenylsulfonyl)-3-(4-methoxy-6-methyl-1,3,5-triazin-2-yl)-3-methylurea(tribenuron-methyl),
1-(2-methoxycarbonylbenzylsulfonyl)-3-(4,6-dimethoxylpyrimidin-2-yl)urea(bensulfuron-methyl),
1-(2-methoxycarbonylphenylsulfonyl)-3-(4,6-bis-(difluoromethoxy)pyrimidin-2-yl)urea(primisulfuron-methyl),
3-(4-ethyl6-methoxy-1,3,5-triazin-2-yl)-1-(2,3-dihydro-1,1-dioxo-2-methylbenzo[b]thiophene-7-sulfonyl)urea (see EP-A-79683),
3-(4-ethoxy-6-ethyl-1,3,5-triazin-2-yl)-1-(2,3-dihydro-1,1-dioxo-2-methylbenzo[b]thiophene-7-sulfonyl)urea (see EP-A-79683),
3-(4-methoxy-6-methyl-1,3,5-triazin-2-yl)-1-(2-methoxycarbonyl-5-iodophenylsulfonyl)urea (see WO 92/13845),
DPX-66037, triflusulfuron-methyl (see Brighton Crop Prot. Conf.—Weeds—1995, p. 853),
CGA-277476, (see Brighton Crop Prot. Conf.—Weeds—1995, p. 79),
methyl 2-[3-(4,6-dimethoxypyrimidin-2-yl)ureidosulfonyl]-4-methane-sulfonamidomethylbenzoate (see WO 95/10507),
N,N-dimethyl-2-[3-(4,6-dimethoxypyrimidin-2-yl) ureidosulfonyl]-4-formyl-aminobenzamide (see PCT/EP 95/01344), B2) thienylsulfonylureas, for example
1-(2-methoxycarbonylthiophen-3-yl)-3-(4-methoxy-6-methyl-1,3,5-triazin-2-yl)urea(thifensulfuron-methyl), B3) pyrazolylsulfonylureas, for example
1-(4-ethoxycarbonyl-1-methylpyrazol-5-yl-sulfonyl)-3-(4,6-dimethoxypyrimidin-2-yl)urea(pyrazosulfuron-methyl),
methyl 3-chloro-5-(4,6-dimethoxypyrimidin-2-ylcarbamoylsulfamoyl)-1-methyl-pyrazole-4-carboxylate (see EP 282613),
methyl 5-(4,6-dimethylpyrimidin-2-ylcarbamoylsulfamoyl)-1-(2-pyridyl)pyrazole-4-carboxylate (NC-330, see Brighton Crop Prot. Conference—Weeds—1991, Vol. 1, p. 45 et seq.),
DPX-A8947, azimsulfuron, (see Brighton Crop Prot. Conf.—Weeds—1995, p. 65), B4) sulfonediamide derivatives, for example
3-(4,6-dimethoxypyrimidin-2-yl)-1-(N-methyl-N-methylsulfonylaminosulfonyl)-urea(amidosulfuron) and structural analogs (see EP-A-131258 and Z. Pfl. Krankh. Pfl. Schutz, Special Issue XII, 489–497 (1990)), B5) pyridylsulfonylureas, for example
1-(3-N,N-dimethylaminocarbonylpyridin-2-ylsulfonyl)-3-(4,6-dimethoxypyrimidin-2-yl)urea(nicosulfuron),
1-(3-ethylsulfonylpyridin-2-ysulfonyl)-3-(-(4,6-dimethoxypyrimidin-2-yl)urea(rimsulfuron),
methyl 2-[3-(4,6-dimethoxypyrimidin-2-yl)ureidosulfonyl]-6-trifluoromethyl-3-pyridinecarboxylate, sodium salt (DPX-KE459, flupyrsulfuron, see Brighton Crop Prot. Conf.—Weeds—1995, p. 49),
pyridylsulfonylureas as they are described in DE-A4000503 and DE-A-4030577, preferably those of the formula

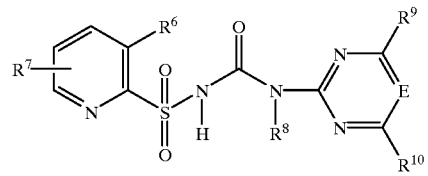

where
E is CH or N, preferably CH,
$R^6$ is iodine or $NR^{11}R^{12}$,
$R^7$ is H, halogen, cyano, $(C_1–C_3)$-alkyl, $(C_1–C_3)$-alkoxy, $(C_1–C_3)$-haloalkyl, $(C_1–C_3)$-haloalkoxy, $(C_1–C_3)$-alkylthio, $(C_1–C_3)$-alkoxy-$(C_1–C_3)$-alkyl, $(C_1–C_3)$-alkoxy-carbonyl, mono- or di-$((C_1–C_3)$-alkyl)amino, $(C_1–C_3)$-alkyl-sulfinyl or -sulfonyl, $SO_2$—$NR^aR^b$ or $CO$—$NR^aR^b$, in particular H,
$R^a$, $R^b$ independently of one another are each H, $(C_1–C_3)$-alkyl, $(C_1–C_3)$-alkenyl, $(C_1–C_3)$-alkynyl or together are —$(CH_2)_4$—, —$(CH_2)_5$— or $(CH_2)_2$—O—$(CH_2)_2$—,
$R^8$ is H or $CH_3$,
$R^9$ is halogen, $(C_1–C_2)$-alkyl, $(C_1–C_2)$-alkoxy, $(C_1–C_2)$-haloalkyl, preferably $CF_3$, $(C_1–C_2)$-haloalkoxy, preferably $OCHF_2$ or $OCH_2CF_3$,
$R^{10}$ is $(C_1–C_2)$-alkyl, $(C_1–C_2)$-haloalkoxy, preferably $OCHF_2$, or $(C_1–C_2)$-alkoxy, and
$R^{11}$ is $(C_1–C_4)$-alkyl and
$R^{12}$ is $(C_1–C_4)$-alkylsulfonyl or
$R^{11}$ and $R^{12}$ together are a chain of the formula —$(CH_2)_3$ $SO_2$— or —$(CH_2)_4SO_2$, for example 3-(4,6-dimethoxypyrimiden-2-yl)-1-(3-N-methylsulfonyl-N-methylaminopyridin- 2-yl) sulfonylurea, or their salts, B6) alkoxyphenoxysulfonylureas, as they are described in EP-A-0342569, preferably those of the formula

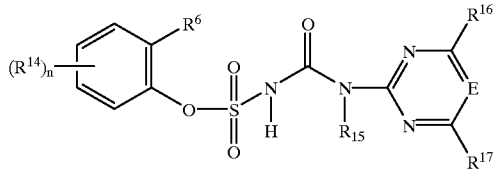

where
- E is CH or N, preferably CH,
- $R^{13}$ is ethoxy, propoxy or isopropoxy,
- $R^{14}$ is hydrogen, halogen, $NO_2$, $CF_3$, CN, $(C_1–C_4)$-alkyl, $(C_1–C_4)$-alkoxy, $(C_1–C_4)$-alkylthio or $((C_1–C_3)$-alkoxy)-carbonyl, preferably in the 6-position on the phenyl ring,
- n is 1, 2 or 3, preferably 1,
- $R^{15}$ is hydrogen, $(C_1–C_4)$-alkyl or $(C_3–C_4)$-alkenyl,
- $R^{16}$, $R^{17}$ independently of one another are each halogen, $(C_1–C_2)$-alkyl, $(C_1–C_2)$-alkoxy, $(C_1–C_2)$-haloalkyl, $(C_1–C_2)$-haloalkoxy or $(C_1–C_2)$-alkoxy-$(C_1–C_2)$-alkyl, preferably $OCH_3$ or $CH_3$,
for example 3-(4,6-dimethoxypyrimidin-2-yl)-1-(2-ethoxyphenoxy)-sulfonylurea, or their salts, B7) imidazolylsulfonylureas, for example
MON 37500, sulfosulfuron (see Brighton Crop Prot. Conf.—Weeds—1995, p. 57), and other related sulfonylurea derivatives and mixtures of these.

C) Cyclohexanedione herbicides such as
methyl 3-(1-allyloxyiminobutyl)-4-hydroxy-6,6-dimethyl-2-oxocyclohex-3-enecarboxylate(alloxydim),
2-(1-ethoximinobutyl)-5-(2-ethylthiopropyl)-3-hydroxycyclohex-2-en-1-one(sethoxydim),
2-(1-ethoximinobutyl)-5-(2-phenylthiopropyl)-3-hydroxycyclohex-2-en-1-one(cloproxydim),
2-(1-(3-chloroallyloxy)iminobutyl)-5-[2-(ethylthio)propyl]-3-hydroxycyclohex-2-en-1-one,
2-(1-(3-chloroallyloxy)iminopropyl)-5-[2-(ethylthio)propyl]-3-hydroxycyclohex-2-en-1-one(clethodim),
2-(1-(ethoxyimino)butyl)-3-hydroxy-5-(thian-3-yl)cyclohex-2-enone(cycloxydim), or
2-(1-ethoxyiminopropyl)-5-(2,4,6-trimethylphenyl)-3-hydroxycyclohex-2-en-1-one(tralkoxydim), D) imidazolinone herbicides such as
methyl 2-(4-isopropyl-4-methyl-5-oxo-2-imidazolin-2-yl)-5-methylbenzoate and
2-(4-isopropyl-4-methyl-5-oxo-2-imidazolin-2-yl)-4-methylbenzoic acid(imazamethabenz),
5-ethyl-2-(4-isopropyl-4-methyl-5-oxo-2-imidazolin-2-yl) pyridine-3-carboxylic acid(imazethapyr),
2-(4-isopropyl-4-methyl-5-oxo-2-imidazolin-2-yl) quinoline-3-carboxylic acid(imazaquin),
2-(4-isopropyl-4-methyl-5-oxo-2-imidazolin-2-yl)pyridine-3-carboxylic acid(imazapyr),
5-methyl-2-(4-isopropyl-4-methyl-5-oxo-2-imidazolin-2-yl)pyridine-3-carboxylic acid(imazethamethapyr), E) triazolopyrimidinesulfonamide derivatives such as
N-(2,6-difluorophenyl)-7-methyl-1,2,4-triazolo-(1,5-c)-pyrimidine-2-sulfonamide(flumetsulam),
N-(2,6-dichloro-3-methylphenyl)-5,7-dimethoxy-1,2,4-triazolo-(1,5-c)-pyrimidine-2-sulfonamide,
N-(2,6-difluorophenyl)-7-fluoro-5-methoxy-1,2,4-triazolo-(1,5-c)-pyrimidine-2-sulfonamide,
N-(2,6-dichloro-3-methylphenyl)-7-chloro-5-methoxy-1,2,4-triazolo-(1,5-c)-pyrimidine-2-sulfonamide,
N-(2-chloro-6-methoxycarbonyl)-5,7-dimethyl-1,2,4-triazolo-(1,5-c)-pyrimidine-2-sulfonamide (see for example EP-A-343 752, U.S. Pat. No. 4,988,812), F) benzoylcyclohexanedione derivatives, for example
2-(2-chloro-4-methylsulfonylbenzoyl)cyclohexane-1,3-dione (SC-0051, see EP-A-137963),
2-(2-nitrobenzoyl)-4,4-dimethylcyclohexane-1,3-dione (see EP-A-274634),
2-(2-nitro-3-methylsulfonylbenzoyl)-4,4-dimethylcyclohexane-1,3-dione (see WO 91/13548), G) pyrimidinyloxypyrimidinecarboxylic acid derivatives or pyrimidinyloxybenzoic acid derivatives, for example
benzyl 3-(4,6-dimethoxypyrimidin-2-yl)oxypyridine-2-carboxylate (EP-A-249 707),
methyl 3-(4,6-dimethoxypyrimidin-2-yl)oxypyridine-2-carboxylate (EP-A-249 707),
2,6-bis[(4,6-dimethoxypyrimidin-2-yl)oxy]benzoic acid (EP-A-321 846),
1-ethoxycarbonyloxyethyl 2,6-bis[(4,6-dimethoxypyrimidin-2-yl)oxy]-benzoate (EP-A472 113) and H) S-(N-aryl-N-alkylcarbamoylmethyl)dithiophosphonic esters such as S-[N-(4-chlorophenyl)-N-isopropylcarbamoylmethyl]O,O-dimethyl dithiophosphate (anilofos).

The abovementioned herbicides from groups A to H are known to those skilled in the art and are, in general, described in "The Pesticide Manual", The British Crop Protection Council and the Royal Soc. of Chemistry, 10th edition, 1994 or in "Agricultural Chemicals Book II—Herbicides—", by W. T. Thompson, Thompson Publications, Fresno Calif., U.S.A. 1990 or in "Farm Chemicals Handbook '90", Meister Publishing Company, Willoughby Ohio, U.S.A. 1990.

The herbicidally active substances and the safeners mentioned can be applied together (as a readymix or by the tank mix method) or one after the other, in any order. The weight ratio of safener:herbicide can vary within wide limits and is preferably in the range from 1:10 to 10:1, in particular 1:10 to 5:1. The amounts of herbicide and safener which are optimal in each case are dependent on the type of the herbicide to be used or on the safener used and on the nature of the plant stand to be treated and can be determined in each individual case by simple preliminary experiments.

The main fields of application for using the safeners are especially cereal crops (wheat, rye, barley, oats, rice, maize, sorghum), but also cotton and soybeans, preferably cereals, particularly preferably maize.

A particular advantage of the safeners of the formula (I) according to the invention is observed when they are combined with herbicides from the group of the sulfonylureas. Some herbicides from this structural class cannot, or not sufficiently selectively, be employed in particular in cereal crops, for example maize. Outstanding selectivities can be achieved in cereals or maize, even in the case of these herbicides, by combining them with the safeners according to the invention.

Depending on their properties, the safeners of the formula (I) can be used for pretreating the seed of the crop plant (seed dressing) or incorporated into the seed furrows before sowing or used together with the herbicide before or after plant emergence. Pre-emergence treatment includes not only the treatment of the area under cultivation prior to sowing, but also treatment of the sown areas under cultivation where growth has not yet taken place. Preferred is the use together with the herbicide. Tank mixes or readymixes can be employed for this purpose.

Depending on the indication and the herbicide used, the application rates of safener required can vary within wide limits and are generally in the range of from 0.001 to 5 kg, preferably 0.005 to 0.5 kg, of active compound per hectare.

The compounds of the formula (I) and their combinations with one or more of the abovementioned herbicides can be formulated in various ways, depending on the biological and/or chemico-physical parameters which are specified. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions or suspensions, suspoemulsions, suspension concentrates (SC), oil- or water-based dispersions, oil-miscible solutions, capsule suspensions (CS), dusts (DP), seed-dressing products, granules for application by broadcasting and soil application, granules (GR) in the form of microgranules, spray granules, coated granules and adsorption granules, granules for soil application or application by broadcasting, water-dipsersible granules (WG), water-soluble granules (SG), ULV formulations, microcapsules and waxes.

These individual formulation types are known in principle and described, for example, in: Winnacker-Küchler, "Chemische Technologie" [chemical technology], Volume 7, C. Hauser Verlag Munich, 4th edition 1986, Wade van Valkenburg, "Pesticide Formulations", Marcel Dekker, New York, 1973; K. Martens, "Spray Drying" Handbook, 3rd edition 1979, G. Goodwin Ltd. London.

The formulation auxiliaries required, such as inert materials, surfactants, solvents and other additives are also known and described, for example, in: Watkins, "Handbook of Insecticide Dust Diluents and Carriers", 2nd edition, Darland Books, Caldwell N.J., H. v. Olphen, "Introduction to Clay Colloid Chemistry"; 2nd edition, J. Wiley & Sons, New York; C. Marsden, "Solvents Guide"; 2nd edition, Interscience, New York 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., New York 1964; Schönfeldt, "Grenzflächenaktive Äthylenoxidaddukte" [surface-active ethylene oxide adducts], Wiss. Verlagsgesell., Stuttgart 1976; Winnacker-Küchler, "Chemische Technologie" [chemical technology], Volume 7, C. Hauser Verlag Munich, 4th edition 1986.

Based on these formulations, it is also possible to prepare combinations with other pesticidally active substances, fertilizers and/or growth regulators, for example in the form of a readymix or a tank mix.

Wettable powders are preparations which are uniformly dispersible in water and which, besides the active substance, also comprise ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalene-sulfonate, or else sodium oleoylmethyltaurinate, in addition to a diluent or inert substance.

Emulsifiable concentrates are prepared by dissolving the active substance in an organic solvent, for example butanol, cyclohexanone, dimethylformamide, xylene, or else higher-boiling aromatics or hydrocarbons, or mixtures of the organic solvents with the addition of one or more ionic and/or nonionic surfactants (emulsifiers). Examples of substances which can be used as emulsifiers are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters, or polyoxyethylene sorbitan esters, for example polyoxyethylene sorbitan fatty acid esters.

Dusts are obtained by grinding the active substance with finely dispersed solid substances, for example, talc, natural clays such as kaolin, bentonite and pyrophyllite, or diatomaceous earth.

Suspension concentrates can be water-based or oil-based. They can be prepared, for example, by wet grinding using commercially available bead mills with or without an addition of surfactants, for example those which have already been mentioned above in the case of the other formulation types.

Emulsions, for example oil-in-water emulsions (EW), can be prepared, for example, by means of stirrers, colloid mills and/or static mixers using aqueous organic solvents in the presence or absence of those surfactants which have already been mentioned above, for example, in the case of the other formulation types.

Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers.

In general, water-dispersible granules are prepared by the customary processes such as spray drying, fluidized-bed granulation, disk granulation, mixing with high-speed mixers, and extrusion without solid inert material.

For the preparation of disk, fluidized-bed, extruder and spray granules see, for example, processes in "Spray-Drying Handbook" 3rd edition, 1979, G. Goodwin Ltd., London; J. E. Browning, "Agglomeration", Chemical and Engineering 1967, pages 147 et seq.; "Perry's Chemical Engineer's Handbook", 5th edition, McGraw-Hill, New York 1973, p. 8–57.

For further details on the formulation of crop protection agents see, for example, G. C. Klingman, "Weed Control as a Science", John Wiley and Sons, Inc., New York, 1961, pages 81–96 and J. D. Freyer, S. A. Evans, "Weed Control Handbook", 5th edition, Blackwell Scientific Publications, Oxford, 1968, pages 101–103.

In general, the agrochemical preparations comprise 0.1 to 99% by weight, in particular 0.1 to 95% by weight, of active substance of the formula (I) (safener) or of the safener/herbicide mixture and 1 to 99.9% by weight, in particular 5 to 99.8% by weight, of a solid or liquid additive and 0 to 25% by weight, in particular 0.1 to 25% by weight, of a surfactant.

In wettable powders, the concentration of active substance is, for example, approximately 10 to 90% by weight, the remainder to 100% by weight being composed of customary formulation components. In the case of emulsifiable concentrates, the concentration of active substance may be approximately 1 to 90, preferably 5 to 80, % by weight. Formulations in the form of dusts comprise 1 to 30% by weight of active substance, in most cases preferably 5 to 20% by weight of active substance; sprayable solutions comprise approximately 0.05 to 80, preferably 2 to 50, % by weight of active substance. In the case of water-dispersible granules, the active substance content depends partly on whether the active compound is in liquid or solid form and on which granulation auxiliaries, fillers and the like are being used. The active substance content of the water-dispersible granules is, for example, between 1 and 95% by weight, preferably between 10 and 80% by weight.

Besides, the abovementioned formulations of active substances may comprise, if appropriate, the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

For use, the formulations which are in commercially available form are, if desired, diluted in the customary manner, for example using water in the case of wettable powders, emulsifiable concentrates, dispersions and water-dispersible granules. Preparations in the form of dusts, granules and sprayable solutions are usually not diluted any further with other inert substances prior to use. The necessary rate of application of the safeners varies with the external conditions such as, inter alia, temperature, humidity and the nature of the herbicide used.

The following examples illustrate the invention:

A. Formulation Examples a) A dust is obtained by mixing 10 parts by weight of a compound of the formula (I) or of an active substance mixture of a herbicide and a safener of the formula (I) and 90 parts by weight of talc as inert substance and comminuting the mixture in a hammer mill.

b) A wettable powder which is readily dispersible in water is obtained by mixing 25 parts by weight of a compound of the formula (I) or of an active substance mixture of a herbicide and a safener of the formula (I), 64 parts by weight of kaolin-containing quartz as inert substance, 10 parts by weight of potassium lignosulfonate and 1 part by weight of sodium oleoylmethyltaurinate as wetting agent and dispersant and grinding the mixture in a pinned-disk mill.

c) A dispersion concentrate which is readily dispersible in water is obtained by mixing 20 parts by weight of a compound of the formula (I) or of an active substance mixture of a herbicide and of a safener of the formula (I) with 6 parts by weight of alkylphenyl polyglycol ether ®Triton X 207), 3 parts by weight of isotridecanol polyglycol ether (8 EO) and 71 parts by weight of paraffinic mineral oil (boiling range, for example, approximately 255 to above 277° C.) and grinding the mixture in a ball mill to a fineness of below 5 microns.

d) An emulsifiable concentrate is obtained from 15 parts by weight of a compound of the formula (I) or of an active substance mixture of a herbicide and a safener of the formula (I), 75 parts by weight of cyclohexanone as solvent and 10 parts by weight of ethoxylated nonylphenol as emulsifier.

e) Water-dispersible granules are obtained by mixing 75 parts by weight of a compound of the formula (I) or of an active substance mixture of a herbicide and a safener of the formula (I),

| 10 parts by weight | of calcium lignosulfonate, |
| 5 parts by weight | of sodium lauryl sulfate, |
| 3 parts by weight | of polyvinyl alcohol and |
| 7 parts by weight | of kaolin, | grinding the mixture in a pinned-disk mill and granulating the powder in a fluidized bed by spraying on water as granulation liquid.

f) Water-dispersible granules are also obtained by homogenizing and precomminuting
25 parts by weight of a compound of the formula (I) or of an active substance mixture of a herbicide and a safener of the formula (I),

| 5 parts by weight | of sodium 2,2'-dinaphthylmethane-6,6'-disulfonate, |
| 2 parts by weight | of sodium oleoylmethyltaurinate, |
| 1 part by weight | of polyvinyl alcohol, |
| 17 parts by weight | of calcium carbonate and |
| 50 parts by weight | of water | in a colloid mill, subsequently grinding the mixture in a bead mill and atomizing and drying the resulting suspension in a spray tower by means of a single-substance nozzle.

B. Preparation Examples

1. Ethyl (E)-2-fluoro-3-(4-chlorophenyl)propenoate

Example 1.1 of Table 1

At −78° C. and under argon, 5.42 g (22.4 mmol) of triethyl 2-fluoro-2-phosphonoacetate are initially charged in 35 ml of THF and admixed with 8.92 ml of a 2.5 M BuLi solution (22.4 mmol). After 30 minutes at this temperature, 2.81 g (20 mmol) of 4-chlorobenzaldehyde—dissolved in 50 ml of THF—are added dropwise. After 2 h at −78° C., the mixture is stirred for a further 5 h at room temperature. Approximately 60 ml of half concentrated HCl are added and the organic phase is separated off, washed with 2×25 ml of saturated NaCl solution and 25 ml of water, dried and concentrated, affording the product as a colorless oil.

Yield: 2.59 g (57%), $^1$H NMR (CDCl$_3$, ppm; TMS): d=1.25 (t, 3H), 4.25 (q, 2H), 6.82 (d, 24 Hz, 1H), 7.35 (dd, 4H)

2. Ethyl (E)-2-fluoro-3-(4-trifluoromethylphenyl)propenoate

Example 1.2 of Table 1

At −78° C. and under argon, 5.33 g (22 mmol) of triethyl 2-fluoro-2-phosphonoacetate are initially charged in 35 ml of THF and admixed with 10 ml of a 2.5 M BuLi solution (26 mmol). After 30 minutes at this temperature, 5.33 g (22 mmol) of 4-trifluoromethylbenzaldehyde—dissolved in 50 ml of THF—are added dropwise. After 2 h at −78° C., the mixture is stirred for a further 5 h at room temperature.

Approximately 60 ml of half concentrated HCl are added and the organic phase is separated off, washed with 2×25 ml of saturated NaCl solution and 25 ml of water, dried and concentrated, affording the product as a resin.

Yield: 4.12 g (71%), $^1$H NMR (d$_6$-DMSO, ppm; TMS): d=1.17 (t, 3H), 4.20 (q, 2H), 7.31 (d, 24 Hz, 1H), 7.72 (dd, 4H)

3. Ethyl (Z)-2-fluoro-3-(4-chlorophenyl)propenoate

Example 2.1 of Table 2

At room temperature, 6 g (26.3 mmol) of the sodium salt of diethyl oxalofluoroacetate are suspended in 200 ml of THF and admixed with 3.7 g (26.3 mmol) of 4-chlorobenzaldehyde. The mixture is heated under reflux for 3 hours and then concentrated, taken up in diethyl ether and stirred with saturated KHCO$_3$ solution. The organic phase is separated off and dried with MgSO$_4$ and the solution is concentrated. Kugelrohr distillation affords the product as a solidified resin.

Yield: 4.5 g (75%), $^1$H NMR (d$_6$-DMSO, ppm; TMS): d=1.31 (t, 3H), 4.32 (q, 2H), 7.10 (d, 36 Hz, 1H), 7.62 (dd, 4H)

4. Ethyl (Z)-2-fluoro-3-(4-trifluoromethylphenyl) propenoate

Example 2.2 of Table 2

At room temperature, 26.2 g (115 mmol) of the sodium salt of diethyl oxalofluoroacetate are suspended in 120 ml of THF and admixed with 20 g (115 mmol) of 4-trifluoromethylbenzaldehyde. The mixture is heated under reflux for 3 hours and then concentrated, taken up in diethyl ether and stirred with saturated KHCO$_3$ solution. The organic phase is separated off and dried with MgSO$_4$ and the solution is concentrated. Kugelrohr distillation affords the product as a solidified resin.

Yield: 21.4 g (71%), $^1$H NMR (d$_6$-DMSO, ppm; TMS): d=1.35 (t, 3H), 4.32 (q, 2H), 7.20 (d, 35 Hz, 1H), 7.85 (dd, 4H)

5. (Z)-2-Fluoro-3-(4-trifluoromethylphenyl)propenoic acid

Example 2.32 of Table 2

At room temperature, 15.0 g (57 mmol) of (Z)-ethyl-2-fluoro-3-(4-trifluoromethylphenyl)propenoate are suspended in 150 ml of methanol and admixed with 21.0 g (0.52 mol) of sodium hydroxide dissolved in 50 ml of water. The mixture is stirred at room temperature for 1 hour, concentrated and adjusted to pH 4 using 2N HCl. The precipitate is filtered off with suction, washed with water and dried.

Yield: 10.8 g (81%), m.p.: 210° C.

6. (Z)-2-Fluoro-3-(4-chlorophenyl)propenoic acid

Example 2.49 of Table 2

At room temperature, 12.8 g (56 mmol) of (Z)-ethyl-2-fluoro-3-(4-chloro-phenyl)propenoate are suspended in 100 ml of methanol and admixed with 21.0 g (0.52 mol) of sodium hydroxide dissolved in 50 ml of water. The mixture is stirred at room temperature for 1 hour, concentrated and adjusted to pH 4 using 2N HCl. The precipitate is filtered off with suction, washed with water and dried.

Yield: 11.5 g (92%), m.p.: 285° C.

7. Butyl (Z)-2-fluoro-3-(4-trifluoromethylphenyl) propenoate

Example 2.34 of Table 2

At room temperature, 5.0 g (19 mmol) of ethyl (Z)-2-fluoro-3-(4-trifluoromethylphenyl)propenoate are initially charged in 40 ml of butanol, admixed with 1 ml of titanium tetraisopropoxide and heated under reflux for 4 h. The reaction mixture is concentrated to dryness under reduced pressure and the crude product is purified by column chromatography (eluent: petroleum ether/ethyl acetate=9/1).

Yield: 4.9 g (89%), $^1$H NMR (CDCl$_3$, ppm, TMS): 0.98 (t, 3H), 1.44 (m, 2H), 1.73 (m, 2H), 4.29 (t, 2H), 6.86 (d, 34 Hz, 1H), 7.38 (dd, 2H), 7.58 (d, 2H)

A series of compounds of the formula (I) which can be obtained in a similar manner are listed by way of example in the tables below:

TABLE 1

Compounds of the formula (Ia)

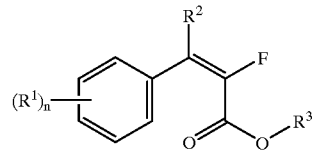

(Ia)

| No. | (R$^1$)$_n$ | R$^2$ | R$^3$ | Physical data ($^1$H NMR) |
|---|---|---|---|---|
| 1.1 | 4-Cl | H | Et | 1.25(t, 3H), 4.25(q, 2H), 6.82 (d, 24Hz, 1H), 7.35(dd, 4H) |
| 1.2 | 4-CF$_3$ | H | Et | 1.17(t, 3H), 4.20(q, 2H), 7.31 (d, 24Hz, 1H), 7.72(dd, 4H) |
| 1.3 | | H | Et | 1.14(t, 3H), 4.19(q, 2H), 7.20 (d, 25Hz, 1H), 7.36(m, 3H), 7.51(m, 2H) |
| 1.4 | 2,4-Di-Cl | H | Et | 1.21(t, 3H), 4.20(q, 2H), 6.87 (d, 20Hz, 1H), 7.22(m, 1H), 7.40(m, 2H) |
| 1.5 | 2,4-Di-F | H | Et | 1.22(t, 3H), 4.24(q, 2H), 6.80 (d, 24Hz, 1H), 6.85(m, 2H), 7.50(m, 1H) |
| 1.6 | 4-F | H | Et | 1.25(t, 3H), 4.23(q, 2H), 6.84 (d, 23Hz, 1H), 7.01(m, 2H), 7.48(m, 2H) |
| 1.7 | 2-F | H | Et | |
| 1.8 | 3-F | H | Et | |
| 1.9 | 2-Cl | H | Et | |
| 1.10 | 3-Cl | H | Et | |
| 1.11 | 3,4-Di-Cl | H | Et | |
| 1.12 | 2,4-Di-F | H | H | |
| 1.13 | 4-OMe | H | Et | |
| 1.14 | 2,4-Di-F | H | CH(CH$_3$)—C$_5$H$_{11}$ | |
| 1.15 | 2,4-Di-F | H | n-Bu | |

TABLE 1-continued

Compounds of the formula (Ia)

$$\text{(R}^1\text{)}_n\text{-C}_6\text{H}_4\text{-C(R}^2\text{)=CF-C(O)-O-R}^3 \quad \text{(Ia)}$$

| No. | $(R^1)_n$ | $R^2$ | $R^3$ | Physical data ($^1$H NMR) |
|---|---|---|---|---|
| 1.16 | 4-CF$_3$ | H | CH(CH$_3$)—C$_5$H$_{11}$ | |
| 1.17 | 4-CF$_3$ | H | n-Bu | |
| 1.18 | 3,4-Di-Cl | H | CH(CH$_3$)—C$_5$H$_{11}$ | |
| 1.19 | 3,4-Di-Cl | H | n-Bu | |
| 1.20 | 4-Me | H | Et | |
| 1.21 | 4-OC$_6$H$_5$ | H | Et | |
| 1.22 | 4-OCF$_2$CF$_2$H | H | Et | |
| 1.23 | 4-C$_6$H$_5$ | H | Et | |
| 1.24 | 4-OCF$_3$ | H | Et | |
| 1.25 | 4-SMe | H | Et | |
| 1.26 | 4-CH(CH$_3$)$_2$ | H | Et | |
| 1.27 | 4-Br | H | Et | |
| 1.28 | 2-CF$_3$ | H | Et | |
| 1.29 | 3-CF$_3$ | H | Et | |
| 1.30 | 4-OCF$_2$H | H | Et | |
| 1.31 | 2-COOMe | H | Et | |
| 1.32 | 4-CF$_3$ | H | H | |
| 1.33 | 4-Br | H | CH(CH$_3$)—C$_5$H$_{11}$ | |
| 1.34 | 4-Cl | H | n-Bu | |
| 1.35 | 4-Cl | H | CH(CH$_3$)—C$_5$H$_{11}$ | |
| 1.36 | 4-Cl | H | H | |
| 1.37 | 4-SO$_2$Me | H | Et | |
| 1.38 | 4-Cl, 3-CF$_3$ | H | Et | |
| 1.39 | 3,4-Di-Br | H | Et | |
| 1.40 | 3,4-Di-Br | H | H | |
| 1.41 | 3,4-Di-Cl | H | Me | |
| 1.42 | 3-Cl | H | H | |
| 1.43 | 2-NO$_2$ | H | Et | |
| 1.44 | 2-NO$_2$, 5-Cl | H | Me | |
| 1.45 | 3,5-Di-Cl | H | Et | |
| 1.46 | 4-Cl | H | Me | |
| 1.47 | 4-CF$_3$ | H | Me | |
| 1.48 | 4-CF$_3$ | H | Pr | |
| 1.49 | 4-CF$_3$ | H | i-Bu | |
| 1.50 | 4-CF$_3$ | H | t-Bu | |
| 1.51 | 4-CF$_3$ | H | (CH$_2$)$_4$—CH$_3$ | |
| 1.52 | 4-CF$_3$ | H | (CH$_2$)$_2$—CH(CH$_3$)$_2$ | |
| 1.53 | 4-CF$_3$ | H | CH(CH$_3$)—(CH$_2$)$_2$—CH$_3$ | |
| 1.54 | 4-CF$_3$ | H | CH$_2$—CH=CH$_2$ | |
| 1.55 | 4-CF$_3$ | H | (CH$_2$)$_2$—O—C$_4$H$_9$ | |
| 1.56 | 4-CF$_3$ | H | CH(CH$_3$)—C$_2$H$_5$ | |
| 1.57 | 4-CF$_3$ | H | (CH$_2$)$_2$—O—C$_2$H$_5$ | |
| 1.58 | 4-CF$_3$ | H | i-C$_8$H$_{17}$ | |
| 1.59 | 4-CF$_3$ | H | Na | salt |
| 1.60 | 4-CF$_3$ | H | K | salt |
| 1.61 | 4-CF$_3$ | H | NH$_4$ | salt |
| 1.62 | 4-CF$_3$ | H | NH$_2$(CH$_3$)$_2$ | salt |
| 1.63 | 4-CF$_3$ | H | NH(C$_2$H$_5$OH)$_3$ | salt |
| 1.64 | 4-CF$_3$ | H | NH$_2$(C$_2$H$_5$OH)$_2$ | salt |
| 1.65 | 4-Cl | H | i-Pr | |
| 1.66 | 4-Cl | H | Pr | |
| 1.67 | 4-Cl | H | i-Bu | |
| 1.68 | 4-Cl | H | t-Bu | |
| 1.69 | 4-Cl | H | (CH$_2$)$_4$—CH$_3$ | |
| 1.70 | 4-Cl | H | (CH$_2$)$_2$—CH(CH$_3$)$_2$ | |
| 1.71 | 4-Cl | H | CH(CH$_3$)—(CH$_2$)$_2$—CH$_3$ | |
| 1.72 | 4-Cl | H | CH$_2$—CH=CH$_2$ | |
| 1.73 | 4-Cl | H | (CH$_2$)$_2$—O—C$_4$H$_9$ | |
| 1.74 | 4-Cl | H | CH(CH$_3$)—C$_2$H$_5$ | |
| 1.75 | 4-Cl | H | (CH$_2$)$_2$—O—C$_2$H$_5$ | |
| 1.76 | 4-Cl | H | i-C$_8$H$_{17}$ | |
| 1.77 | 4-Cl | H | Na | salt |
| 1.78 | 4-Cl | H | K | salt |
| 1.79 | 4-Cl | H | NH$_4$ | salt |
| 1.80 | 4-Cl | H | NH$_2$(CH$_3$)$_2$ | salt |

TABLE 1-continued

Compounds of the formula (Ia)

$$\text{(R}^1)_n-\text{C}_6\text{H}_4-\text{C}(\text{R}^2)=\text{C}(\text{F})-\text{C}(=\text{O})-\text{O}-\text{R}^3 \quad \text{(Ia)}$$

| No. | $(R^1)_n$ | $R^2$ | $R^3$ | Physical data ($^1$H NMR) |
|---|---|---|---|---|
| 1.81 | 4-Cl | H | NH($C_2H_5$OH)$_3$ | salt |
| 1.82 | 4-Cl | H | NH$_2$($C_2H_5$OH)$_2$ | salt |
| 1.83 | 3,4-Di-Cl | H | Pr | |
| 1.84 | 3,4-Di-Cl | H | i-Bu | |
| 1.85 | 3,4-Di-Cl | H | t-Bu | |
| 1.86 | 3,4-Di-Cl | H | (CH$_2$)$_4$—CH$_3$ | |
| 1.87 | 3,4-Di-Cl | H | (CH$_2$)$_2$—CH(CH$_3$)$_2$ | |
| 1.88 | 3,4-Di-Cl | H | CH(CH$_3$)—(CH$_2$)$_2$—CH$_3$ | |
| 1.89 | 3,4-Di-Cl | H | CH$_2$—CH=CH$_2$ | |
| 1.90 | 3,4-Di-Cl | H | (CH$_2$)$_2$—O—C$_4$H$_9$ | |
| 1.91 | 3,4-Di-Cl | H | CH(CH$_3$)—C$_2$H$_5$ | |
| 1.92 | 3,4-Di-Cl | H | (CH$_2$)$_2$—O—C$_2$H$_5$ | |
| 1.93 | 3,4-Di-Cl | H | i-C$_8$H$_{17}$ | |
| 1.94 | 3,4-Di-Cl | H | Na | salt |
| 1.95 | 3,4-Di-Cl | H | K | salt |
| 1.96 | 3,4-Di-Cl | H | NH$_4$ | salt |
| 1.97 | 3,4-Di-Cl | H | NH$_2$(CH$_3$)$_2$ | salt |
| 1.98 | 3,4-Di-Cl | H | NH($C_2H_5$OH)$_3$ | salt |
| 1.99 | 3,4-Di-Cl | H | NH$_2$($C_2H_5$OH)$_2$ | salt |
| 1.100 | 3,4-Di-Cl | H | i-Pr | |
| 1.101 | 4-CF$_3$ | H | i-Pr | |
| 1.102 | 2,4-Di-Cl | H | H | |
| 1.103 | 2,4-Di-Cl | H | (CH$_2$)$_2$—OMe | |
| 1.104 | 2,4-Di-Cl | H | n-Bu | |
| 1.105 | 2,4-Di-Cl | H | i-Bu | |
| 1.106 | 2,4-Di-Cl | H | (CH$_2$)$_2$—OC$_2$H$_5$ | |
| 1.107 | 3,4-Di-Cl | H | (CH$_2$)$_2$—OMe | |

TABLE 2

Compounds of the formula (Ib)

$$\text{(R}^1)_n-\text{C}_6\text{H}_4-\text{C}(\text{R}^2)=\text{C}(\text{F})-\text{C}(=\text{O})-\text{O}-\text{R}^3 \quad \text{(Ib)}$$

| No. | $(R^1)_n$ | $R^2$ | $R^3$ | Phys. data ($^1$H NMR, b.p., etc.) |
|---|---|---|---|---|
| 2.1 | 4-Cl | H | Et | 1.31(t, 3H), 4.32(q, 2H), 7.10(d, 36Hz, 1H), 7.62(dd, 4H) |
| 2.2 | 4-CF$_3$ | H | Et | 1.35(t, 3H), 4.32(q, 2H), 7.20(d, 35Hz, 1H), 7.85(dd, 4H) |
| 2.3 | H | H | Et | b.p.: 143° C. (19 mbar) |
| 2.4 | 2,4-Di-Cl | H | Et | 1.35(t, 3H), 4.37(q, 2H), 7.20(d, 35Hz, 1H), 7.50(m, 2H), 7.85(m, 1H) |
| 2.5 | 2,4-Di-F | H | Et | 1.40(t, 3H), 4.38(q, 2H), 6.90(m, 2H), 7.15(d, 35Hz, 1H), 7.92(m, 1H) |
| 2.6 | 4-F | H | Et | 1.31(t, 3H), 4.32(q, 2H), 7.10(d, 36Hz, 1H), 7.34(m, 2H), 7.80(m, 2H) |
| 2.7 | 2-F | H | Et | 1.32(t, 3H), 4.32(q, 2H), 7.10(d, 38Hz, 1H), 7.35(m, 2H), 7.52, (m, 1H), 7.85(m, 1H) |
| 2.8 | 3-F | H | Et | 1.31(t, 3H), 4.32(q, 2H), 7.13(d, 38Hz, 1H), 7.28(m, 1H), 7.57(m, 2H) |
| 2.9 | 2-Cl | H | Et | 1.32(t, 3H), 4.35(q, 2H), 7.25(d, 38Hz, 1H), 7.47(m, 2H), 7.60(m, 1H), 7.85(m, 1H) |
| 2.10 | 3-Cl | H | Et | 1.31(t, 3H), 4.31(q, 2H), 7.10(d, 35Hz, 1H), 7.50(m, 2H), 7.68(m, 1H), 7.75(s, 1H) |

TABLE 2-continued

Compounds of the formula (Ib)

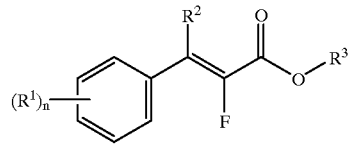

(Ib)

| No. | $(R^1)_n$ | $R^2$ | $R^3$ | Phys. data ($^1$H NMR, b.p., etc.) |
|---|---|---|---|---|
| 2.11 | 3,4-Di-Cl | H | Et | 1.30(t, 3H), 4.30(q, 2H), 7.18(d, 38Hz, 1H), 7.75(d, 2H), 7.98(s, 1H) |
| 2.12 | 2,4-Di-F | H | H | 6.80(d, 36Hz, 1H), 7.15(m, 1H), 7.32 (m, 1H), 7.85(m, 1H) |
| 2.13 | 4-OMe | H | Et | 1.30(t, 3H), 3.80(s, 3H), 4.25(q, 2H), 7.02(d, 38Hz, 1H), 7.03(d, 2H), 7.67(d, 2H) |
| 2.14 | 2,4-Di-F | H | CH(CH$_3$)—C$_5$H$_{11}$ | $n_D$: 1.4680 (21° C.) |
| 2.15 | 2,4-Di-F | H | n-Bu | 0.92(t, 3H), 1.40(m, 2H), 1.70(m, 2H), 4.28(t, 2H), 7.00(d, 35Hz, 1H), 7.20 (m, 1H), 7.37(m, 1H), 7.90(m, 1H) |
| 2.16 | 4-CF$_3$ | H | CH(CH$_3$)—C$_5$H$_{11}$ | $n_D$: 1.4720 (23° C.) |
| 2.17 | 4-CF$_3$ | H | n-Bu | 0.98(t, 3H), 1.45(m, 2H), 1.72(m, 2H), 4.31(t, 2H), 6.92(d, 32Hz, 1H), 7.70(dd, 4H) |
| 2.18 | 3,4-Di-Cl | H | CH(CH$_3$)—C$_5$H$_{11}$ | $n_D$: 1.5147 (22° C.) |
| 2.19 | 3,4-Di-Cl | H | n-Bu | 0.98(t, 3H), 1.43(m, 2H), 1.72(m, 2H), 4.30(t, 2H), 6.80(d, 33Hz, 1H), 7.48(d, 2H) 7.73(s, 1H) |
| 2.20 | 4-Me | H | Et | $n_D$: 1.5428(23° C.) |
| 2.21 | 4-OC$_6$H$_5$ | H | Et | 1.32(t, 3H), 4.32(q, 2H), 6.88(d, 35Hz, 1H), 7.10(m, 5H), 7.35(d, 2H), 7.60(d, 2H) |
| 2.22 | 4-OCF$_2$-CF$_2$H | H | Et | 1.38,(t, 3H), 4.38(q, 2H), 5.92(tt, 1H), 6.90(d, 35Hz, 1H), 7.22(d, 2H), 7.65(d, 2H) |
| 2.23 | 4-C$_6$H$_5$ | H | Et | 1.37(t, 3H), 4.30(q, 2H), 6.92(d, 35Hz, 1H), 7.4(m, 3H), 7.6(m, 6H) |
| 2.24 | 4-OCF$_3$ | H | Et | 1.40(t, 3H), 4.37(q, 2H), 6.90(d, 33Hz, 1H), 7.22(d, 2H), 7.65(d, 2H) |
| 2.25 | 4-SMe | H | Et | 1.39(t, 3H), 2.48(s, 3H), 4.32(q, 2H), 6.85(d, 38Hz, 1H), 7.22(d, 2H), 7.55(d, 2H) |
| 2.26 | 4-CH(CH$_3$)$_2$ | H | Et | 1.22(d, 6H), 1.38(t, 3H), 2.90(m, 1H), 4.35(q, 2H), 6.90(q, 36Hz, 1H), 7.25 (d, 2H), 7.60(d, 2H) |
| 2.27 | 4-Br | H | Et | 1.38(t, 3H), 4.32(q, 2H), 6.87(d, 38Hz, 1H), 7.50(m, 4H) |
| 2.28 | 2-CF$_3$ | H | Et | $n_D$: 1.4782 (25° C.) |
| 2.29 | 3-CF$_3$ | H | Et | 1.39(t, 3H), 4.37(q, 2H), 6.92(d, 32Hz, 1H), 7.57(m, 2H), 7.83(m, 2H) |
| 2.30 | 4-OCF$_2$H | H | Et | 1.39(t, 3H), 4.35(q, 2H), 6.59(t, 71Hz, 1H), 6.90(d, 33Hz, 1H), 7.15(d, 2H), 7.63(d, 2H) |
| 2.31 | 2-COOMe | H | Et | 1.40(t, 3H), 3.92(s, 3H), 4.38(q, 2H), 7.41(t, 1H), 7.58(t, 1H), 7.80(d, 35Hz, 1H), 7.82(d, 2H), 8.03(d, 2H) |
| 2.32 | 4-CF$_3$ | H | H | m.p.: 210° C. |
| 2.33 | 4-Br | H | CH(CH$_3$)—C$_5$H$_{11}$ | $n_D$: 1.5058 (22° C.) |
| 2.34 | 4-Cl | H | n-Bu | 0.98(t, 3H), 1.44(m, 2H), 1.73(m, 2H), 4.29(t, 2H), 6.86(d, 34Hz, 1H), 7.38 (dd, 2H), 7.58(d, 2H) |
| 2.35 | 4-Cl | H | CH(CH$_3$)—C$_5$H$_{11}$ | $n_D$: 1.5109 (26° C.) |
| 2.36 | 4-OCF$_3$ | H | CH(CH$_3$)—C$_5$H$_{11}$ | |
| 2.37 | 4-OCF$_2$H | H | CH(CH$_3$)—C$_5$H$_{11}$ | |
| 2.38 | 4-OCF$_3$ | H | n-Bu | |
| 2.39 | 4-OCF$_2$H | H | n-Bu | |
| 2.40 | 4-OMe | H | n-Bu | |
| 2.41 | 3,4-Di-Cl | H | Me | 3.90(s, 3H), 6.83(d, 35Hz, 1H), 7.43 (s, 2H), 7.75(s, 1H) |
| 2.42 | 4-Cl | H | Me | |
| 2.43 | 4-CF$_3$ | H | i-Pr | |
| 2.44 | 2,4-Di-Cl | H | Me | |
| 2.45 | 4-F | H | Me | |
| 2.46 | 4-F | H | n-Bu | |
| 2.47 | 4-F | H | H | |
| 2.48 | 4-F | H | CH(CH$_3$)—C$_5$H$_{11}$ | |
| 2.49 | 4-Cl | H | H | m.p.: 285° C. |
| 2.50 | 4-SO$_2$Me | H | Et | m.p.: 115° C. |
| 2.51 | 4-Cl, 3-CF$_3$ | H | Et | 1.40(t, 3H), 437(t, 2H), 6.90(d, 34Hz, |

TABLE 2-continued

Compounds of the formula (Ib)

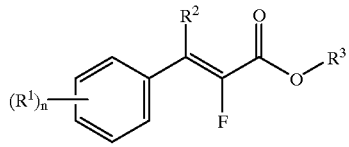

(Ib)

| No. | $(R^1)_n$ | $R^2$ | $R^3$ | Phys. data ($^1$H NMR, b.p., etc.) |
|---|---|---|---|---|
| | | | | 1H), 7.60(d, 1H), 7.77(d, 1H), 7.86(s, 1H) |
| 2.52 | 3,4-Di-Br | H | Et | |
| 2.53 | 3,4-Di-Br | H | H | |
| 2.54 | 3,4-Di-Cl | H | i-Pr | |
| 2.55 | 3-Cl | H | H | |
| 2.56 | 2-NO$_2$ | H | Et | |
| 2.57 | 2-NO$_2$, 5-Cl | H | Me | |
| 2.58 | 3,5-Di-Cl | H | Et | |
| 2.59 | 4-Cl | Me | Et | |
| 2.60 | 4-Cl | Me | H | |
| 2.61 | 4-Cl | Me | CH(CH$_3$)—C$_5$H$_{11}$ | |
| 2.62 | 4-Cl | Me | n-Bu | |
| 2.63 | 4-CF$_3$ | Me | Et | |
| 2.64 | 4-CF$_3$ | Me | H | |
| 2.65 | 4-CF$_3$ | Me | CH(CH$_3$)—C$_5$H$_{11}$ | |
| 2.66 | 4-CF$_3$ | Me | n-Bu | |
| 2.67 | 3,4-Di-Cl | Me | Et | |
| 2.68 | 3,4-Di-Cl | Me | H | |
| 2.69 | 3,4-Di-Cl | Me | CH(CH$_3$)—C$_5$H$_{11}$ | |
| 2.70 | 3,4-Di-Cl | Me | n-Bu | |
| 2.71 | 2,4-Di-Cl | Me | Et | |
| 2.72 | 2,4-Di-Cl | Me | H | |
| 2.73 | 2,4-Di-Cl | Me | CH(CH$_3$)—C$_5$H$_{11}$ | |
| 2.74 | 2,4-Di-Cl | Me | n-Bu | |
| 2.75 | 4-CF$_3$ | H | (CH$_2$)$_2$—OMe | $n_D$: 1.4881 (25° C.) |
| 2.76 | 4-CF$_3$ | H | Me | 3.90(s, 3H), 6.95(d, 34Hz, 1H), 7.65 (d, 2H), 7.75(d, 2H) |
| 2.77 | 4-NO$_2$ | H | Et | m.p.: 130° C. |
| 2.78 | 3,4-Di-OMe | H | Et | 1.39(t, 3H), 3.90(s, 3H), 3.92(s, 3H), 4.35(q, 2H), 6.85(d, 35Hz, 1H), 6.90 (d, 1H), 7.20(d, 1H), 7.24(s, 1H) |
| 2.79 | 4-F-3-OPh | H | Et | 1.38(t, 3H), 4.37(q, 2H), 6.80(d, 34Hz, 1H), 7.00(d, 1H), 7.20(m, 2H), 7.39(m, 5H) |
| 2.80 | 3-OPh | H | Et | $n_D$: 1.5748 (22° C.) |
| 2.81 | 3-OMe-4-OCH$_2$—O-5 | H | Et | 1.30(t, 3H), 3.82(s, 3H), 4.25(q, 2H), 6.08(s, 2H), 7.00(d, 34Hz, 1H), 6.98 (s, 1H), 7.05(s, 1H) |
| 2.82 | 3-O—(CH$_2$)$_2$—O-4 | H | Et | 1.35(t, 3H), 4.25(s, br, 4H), 4.30(q, 2H), 6.80(d, 35Hz, 1H), 6.85(d, 1H), 7.10(dd, 1H), 7.20(d, 1H) |
| 2.83 | 4-Cl-3-F | H | Et | 1.40(t, 3H), 4.38(q, 2H), 6.83(d, 34Hz, 1H), 7.30(d, 1H), 7.42(m, 2H) |
| 2.84 | 3-O—CH$_2$—O-4 | H | Et | m.p.: 88° C. |
| 2.85 | 3-O—CH$_2$—O-4 | H | H | m.p.: 290° C. |
| 2.86 | 2-F-4-CF$_3$ | H | (CH$_2$)$_2$—OMe | $n_D$: 1.4761 (23° C.) |
| 2.87 | 2-F-4-CF$_3$ | H | Et | $n_D$: 1.4765 (24° C.) |
| 2.88 | 3,4-Di-Cl | H | H | m.p.: 215° C. |
| 2.89 | 4-O-tBu | H | Et | $n_D$: 1.5249 |
| 2.90 | 4-CF$_3$ | H | Pr | |
| 2.91 | 4-CF$_3$ | H | i-Bu | |
| 2.92 | 4-CF$_3$ | H | t-Bu | |
| 2.93 | 4-CF$_3$ | H | (CH$_2$)$_4$—CH$_3$ | |
| 2.94 | 4-CF$_3$ | H | (CH$_2$)$_2$—CH(CH$_3$)$_2$ | |
| 2.95 | 4-CF$_3$ | H | CH(CH$_3$)—(CH$_2$)$_2$—CH$_3$ | |
| 2.96 | 4-CF$_3$ | H | CH$_2$—CH=CH$_2$ | |
| 2.97 | 4-CF$_3$ | H | (CH$_2$)$_2$—O—C$_4$H$_9$ | |
| 2.98 | 4-CF$_3$ | H | CH(CH$_3$)—C$_2$H$_5$ | |
| 2.99 | 4-CF$_3$ | H | (CH$_2$)$_2$—O—C$_2$H$_5$ | |
| 2.100 | 4-CF$_3$ | H | i-C$_8$H$_{17}$ | |
| 2.101 | 4-CF$_3$ | H | Na | salt |
| 2.102 | 4-CF$_3$ | H | K | salt |
| 2.103 | 4-CF$_3$ | H | NH$_4$ | salt |
| 2.104 | 4-CF$_3$ | H | NH$_2$(CH$_3$)$_2$ | salt |
| 2.105 | 4-CF$_3$ | H | NH(C$_2$H$_5$OH)$_3$ | salt |
| 2.106 | 4-CF$_3$ | H | NH$_2$(C$_2$H$_5$OH)$_2$ | salt |

TABLE 2-continued

Compounds of the formula (Ib)

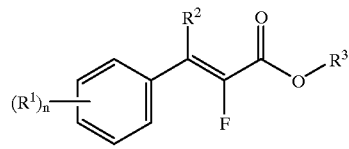
(Ib)

| No. | $(R^1)_n$ | $R^2$ | $R^3$ | Phys. data ($^1$H NMR, b.p., etc.) |
|---|---|---|---|---|
| 2.107 | 4-Cl | H | i-Pr | |
| 2.108 | 4-Cl | H | Pr | |
| 2.109 | 4-Cl | H | i-Bu | |
| 2.110 | 4-Cl | H | t-Bu | |
| 2.111 | 4-Cl | H | $(CH_2)_4$—$CH_3$ | |
| 2.112 | 4-Cl | H | $(CH_2)_2$—$CH(CH_3)_2$ | |
| 2.113 | 4-Cl | H | $CH(CH_3)$—$(CH_2)_2$—$CH_3$ | |
| 2.114 | 4-Cl | H | $CH_2$—$CH$=$CH_2$ | |
| 2.115 | 4-Cl | H | $(CH_2)_2$—O—$C_4H_9$ | |
| 2.116 | 4-Cl | H | $CH(CH_3)$—$C_2H_5$ | |
| 2.117 | 4-Cl | H | $(CH_2)_2$—O—$C_2H_5$ | |
| 2.118 | 4-Cl | H | $i$-$C_8H_{17}$ | |
| 2.119 | 4-Cl | H | Na | salt |
| 2.120 | 4-Cl | H | K | salt |
| 2.121 | 4-Cl | H | $NH_4$ | salt |
| 2.122 | 4-Cl | H | $NH_2(CH_3)_2$ | salt |
| 2.123 | 4-Cl | H | $NH(C_2H_5OH)_3$ | salt |
| 2.124 | 4-Cl | H | $NH_2(C_2H_5OH)_2$ | salt |
| 2.125 | 3,4-Di-Cl | H | Pr | |
| 2.126 | 3,4-Di-Cl | H | i-Bu | |
| 2.127 | 3,4-Di-Cl | H | t-Bu | |
| 2.128 | 3,4-Di-Cl | H | $(CH_2)_4$—$CH_3$ | |
| 2.129 | 3,4-Di-Cl | H | $(CH_2)_2$—$CH(CH_3)_2$ | |
| 2.130 | 3,4-Di-Cl | H | $CH(CH_3)$—$(CH_2)_2$—$CH_3$ | |
| 2.131 | 3,4-Di-Cl | H | $CH_2$—$CH$=$CH_2$ | |
| 2.132 | 3,4-Di-Cl | H | $(CH_2)_2$—O—$C_4H_9$ | |
| 2.133 | 3,4-Di-Cl | H | $CH(CH_3)$—$C_2H_5$ | |
| 2.134 | 3,4-Di-Cl | H | $(CH_2)_2$—O—$C_2H_5$ | |
| 2.135 | 3,4-Di-Cl | H | $i$-$C_8H_{17}$ | |
| 2.136 | 3,4-Di-Cl | H | Na | salt |
| 2.137 | 3,4-Di-Cl | H | K | salt |
| 2.138 | 3,4-Di-Cl | H | $NH_4$ | salt |
| 2.139 | 3,4-Di-Cl | H | $NH_2(CH_3)_2$ | salt |
| 2.140 | 3,4-Di-Cl | H | $NH(C_2H_5OH)_3$ | salt |
| 2.141 | 3,4-Di-Cl | H | $NH_2(C_2H_5OH)_2$ | salt |
| 2.142 | 2-F-4-$CF_3$ | H | H | |
| 2.143 | 2-F-4-$CF_3$ | H | Me | |
| 2.144 | 2-F-4-$CF_3$ | H | Pr | |
| 2.145 | 2-F-4-$CF_3$ | H | i-Pr | |
| 2.146 | 2-F-4-$CF_3$ | H | n-Bu | |
| 2.147 | 2-F-4-$CF_3$ | H | i-Bu | |
| 2.148 | 2-F-4-$CF_3$ | H | t-Bu | |
| 2.149 | 2-F-4-$CF_3$ | H | $(CH_2)_4$—$CH_3$ | |
| 2.150 | 2-F-4-$CF_3$ | H | $(CH_2)_2$—$CH(CH_3)_2$ | |
| 2.151 | 2-F-4-$CF_3$ | H | $CH(CH_3)$—$(CH_2)_2$—$CH_3$ | |
| 2.152 | 2-F-4-$CF_3$ | H | $CH_2$—$CH$=$CH_2$ | |
| 2.153 | 2-F-4-$CF_3$ | H | $(CH_2)_2$—O—$C_4H_9$ | |
| 2.154 | 2-F-4-$CF_3$ | H | $CH(CH_3)$—$C_2H_5$ | |
| 2.155 | 2-F-4-$CF_3$ | H | $(CH_2)_2$—O—$C_2H_5$ | |
| 2.156 | 2-F-4-$CF_3$ | H | $i$-$C_8H_{17}$ | |
| 2.157 | 2-F-4-$CF_3$ | H | Na | salt |
| 2.158 | 2-F-4-$CF_3$ | H | K | salt |
| 2.159 | 2-F-4-$CF_3$ | H | $NH_4$ | salt |
| 2.160 | 2,4-Di-Cl | H | $(CH_2)_2$—OMe | |
| 2.161 | 2,4-Di-Cl | H | $(CH_2)_2$—$OC_2H_5$ | |
| 2.162 | 2,4-Di-Cl | H | i-Bu | |
| 2.163 | 3,4-Di-Cl | H | $(CH_2)_2$—OMe | |
| 2.164 | 4-$CF_3$ | H | N=$C(CH_3)_2$ | 2.12(s, 6H); 7.05(d, 35Hz, 1H); 7.71(dd, 4H) |
| 2.165 | 4-$CO_2$Me | H | Et | 1.40(t, 3H); 3.92(s, 3H); 4.38(q, 2H); 6.95(d, 34Hz, 1H); 7.70(d, 2H); 8.07(d, 2H) |
| 2.166 | 4-$CF_3$ | H | N=$CHCH_3$ | 2.11(s, 3H); 7.05(d, 34Hz, 1H); 7.70 (dd, 4H); 7.95(q, 1H) |

TABLE 3

Compounds of the formula (Ic)

(Ic)

| No. | $(R^1)_n$ | $R^2$ | $R^3$ | Phys. data ($^1$H NMR, b.p., etc.) |
|---|---|---|---|---|
| 3.1 | 6-Cl | H | Et | m.p.: 70° C. |
| 3.2 | H | H | Et | $n_D$: 1.5375 (25° C.) |
| 3.3 | 6-Cl | H | Me | |
| 3.4 | H | H | Me | |
| 3.5 | 6-Cl | H | n-Bu | |
| 3.6 | H | H | n-Bu | |
| 3.7 | 6-Cl | H | CH(CH$_3$)—C$_5$H$_{11}$ | |
| 3.8 | H | H | CH(CH$_3$)—C$_5$H$_{11}$ | |
| 3.9 | 2-Me | H | Et | |
| 3.10 | 2-Me | H | Me | |
| 3.11 | 2-Me | H | n-Bu | |
| 3.12 | 2-Me | H | CH(CH$_3$)—C$_5$H$_{11}$ | |
| 3.13 | 6-Cl | H | H | m.p.: 229° C. |
| 3.14 | 6-Cl | H | Pr | |
| 3.15 | 6-Cl | H | i-Pr | |
| 3.16 | 6-Cl | H | i-Bu | |
| 3.17 | 6-Cl | H | t-Bu | |

TABLE 4

Compounds of the formula (Id)

(Id)

| No. | $(R^1)_n$ | $R^2$ | $R^3$ | Phys. data ($^1$H NMR, b.p., etc.) |
|---|---|---|---|---|
| 4.1 | H | H | Et | 1.40(t, 3H), 4.39(d, 2H), 6.85(d, 35 Hz, 1H), 7.48(d, 2H), 8.68(d, 2H) |
| 4.2 | H | H | Me | |
| 4.3 | H | H | n-Bu | |
| 4.4 | H | H | CH(CH$_3$)—C$_5$H$_{11}$ | |
| 4.5 | 2,6-Di-Cl | H | Et | |
| 4.6 | 2,6-Di-Cl | H | Me | |
| 4.7 | 2,6-Di-Cl | H | n-Bu | |
| 4.8 | 2,6-Di-Cl | H | CH(CH$_3$)—C$_5$H$_{11}$ | |

TABLE 5

Compounds of the formula (Ie)

(Ie)

| No. | $(R^1)_n$ | $R^2$ | $R^3$ | Phys. data ($^1$H NMR etc.) |
|---|---|---|---|---|
| 5.1 | H | H | Et | $n_D$: 1.5261 (23° C.) |
| 5.2 | H | H | Me | |
| 5.3 | H | H | n-Bu | |
| 5.4 | H | H | CH(CH$_3$)—C$_5$H$_{11}$ | |
| 5.5 | 6-Me | H | Et | $n_D$: 1.5260 (23° C.) |
| 5.6 | 6-Me | H | Me | |
| 5.7 | 6-Me | H | n-Bu | |
| 5.8 | 6-Me | H | CH(CH$_3$)—C$_5$H$_{11}$ | |
| 5.9 | 3-Cl-5-CF$_3$ | H | Et | 1.40(t, 3H), 4.41(q, 2H) 7.38(d, 36 Hz, 1H), 8.00(s, 1H), 8.86(s, 1H) |
| 5.10 | 3-Cl-5-CF$_3$ | H | Me | |
| 5.11 | 3-Cl-5-CF$_3$ | H | n-Bu | |
| 5.12 | 3-Cl-5-CF$_3$ | H | CH(CH$_3$)—C$_5$H$_{11}$ | |
| 5.13 | H | H | H | m.p.: 150° C. |

Abbreviations in Tables 1-5:
Me = CH$_3$, Et = C$_2$H$_5$, Pr = C$_3$H$_7$ = n-propyl, i-Pr = isopropyl, Bu = C$_4$H$_9$ = n-butyl, i-Bu = isobutyl, t-Bu = tert-butyl,
b.p. = boiling point, m.p. = melting point, $n_D$ = refractive index stated as the refractive index for the sodium D line.
If $(R^1)_n$ = H then this corresponds to the unsubstituted case (n = 0).

C. Biological Examples

Seeds of barley, rice or maize were placed in plastic pots in sandy loam, grown to the 3- to 4-leaf stage in the greenhouse and treated successively with the compounds according to the invention and the herbicides, by the post-emergence method. The herbicides and the compounds of the formula (I) were applied in form of aqueous suspensions or emulsions in an application rate of 300 l of water/ha (converted). 3–4 weeks after the treatment, the plants were scored visually for any kind of damage by the herbicides which had been applied, particularly taking into account the extent of lasting growth inhibition. The results were evaluated in percentages in comparison to untreated controls. Some test results are listed in Tables 6, 7 and 8:

TABLE 6

Effect of safener in barley

| Product herbicide/safener | Doses (kg of a.i./ha) | Herbicidal activity in % HORVU |
|---|---|---|
| H$_1$ | 0.2 | 80 |
| H$_1$ + No. 2.41 | 0.2 + 1.25 | 35 |
| H$_1$ + No. 2.3 | 0.2 + 1.25 | 55 |
| H$_1$ + No. 2.5 | 0.2 + 1.25 | 60 |
| H$_1$ + No. 2.6 | 0.2 + 1.25 | 45 |
| H$_1$ + No. 1.2 | 0.2 + 1.25 | 60 |
| H$_1$ + No. 2.1 | 0.2 + 1.25 | 30 |
| H$_1$ + No. 2.4 | 0.2 + 1.25 | 20 |
| H$_1$ + No. 2.11 | 0.2 + 1.25 | 25 |

H$_1$ = fenoxaprop-ethyl
HORVU = Hordeum vulgare (barley)
No. ... = Safener of Example No. ... from Section B (Chemical Examples)

TABLE 7

Effect of safener in rice

| Product herbicide/safener | Doses (kg of a.i./ha) | Herbicidal activity in % ORYSA |
|---|---|---|
| $H_1$ | 0.3 | 85 |
| $H_1$ + No. 2.41 | 0.3 + 1.25 | 65 |
| $H_1$ + No. 2.56 | 0.3 + 1.25 | 65 |
| $H_1$ + No. 2.27 | 0.3 + 1.25 | 65 |

$H_1$ = fenoxaprop-ethyl
ORYSA = Oryza sativa (rice)
No. ... = Safener of Example No. ... from Section B (Chemical Examples)

TABLE 8

Effect of safener in maize

| Product herbicide/safener | Doses (kg of a.i./ha) | Herbicidal activity in % ZEAMA |
|---|---|---|
| $H_2$ | 0.075 | 90 |
| $H_2$ + No. 2.41 | 0.075 + 1.25 | 50 |
| $H_2$ + No. 2.27 | 0.075 + 1.25 | 65 |
| $H_2$ + No. 1.02 | 0.075 + 1.25 | 45 |
| $H_2$ + No. 2.01 | 0.075 + 1.25 | 60 |
| $H_2$ + No. 2.02 | 0.075 + 1.25 | 40 |
| $H_2$ + No. 2.17 | 0.075 + 1.25 | 45 |
| $H_2$ + No. 2.16 | 0.075 + 1.25 | 40 |

$H_2$ = 3-(4,6-dimethoxypyrimidin-2-yl)-1-[3-(N-methyl-N-methylsulfonylamino)-2-pyridylsulfonyl]urea
ZEAMA = Zea mays (maize)
No. ... = Safener of Example No. ... from Section B (Chemical Examples)

We claim:

1. A herbicide/safener combination, which comprises
A) at least one herbicidally active compound and
B) at least one compound of the formula (I)

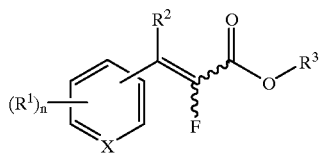

(I)

in which

X is CH or N;

n, in the case that X=N, is an integer from 0 to 4 and, in the case that X=CH, is an integer from 0 to 5;

$R^1$ is halogen, $(C_1-C_8)$-alkyl, $(C_2-C_8)$-alkenyl, $(C_2-C_8)$-alkynyl, $(C_3-C_6)$-cycloalkyl, $(C_5-C_6)$-cycloalkenyl, aryl, $(C_1-C_8)$-alkoxy, $(C_2-C_8)$-alkenyloxy, $(C_2-C_8)$-alkynyloxy, phenoxy, sulfamoyl, amino, mono- or di-$(C_1-C_4)$-alkylamino, nitro, hydroxyl, mono- or di-$(C_1-C_4)$-alkylaminosulfonyl, cyano, $(C_1-C_8)$-alkylthio, $(C_1-C_8)$-alkylsulfinyl, $(C_1-C_8)$-alkylsulfonyl, $(C_1-C_8)$-alkoxycarbonyl, $(C_1-C_8)$-alkylthiocarbonyl or $(C_1-C_8)$-alkylcarbonyl, where each of the abovementioned carbon-containing radicals is unsubstituted or substituted by one or more identical or different radicals selected from the group consisting of halogen, halo-$(C_1-C_8)$-alkoxy, phosphoryl, nitro, amino, mono- or di-$(C_1-C_4)$-alkylamino, cyano, hydroxyl and $(C_1-C_8)$-alkoxy where one or more $CH_2$ groups may be replaced by oxygen and, in the case of cyclic radicals, also of $(C_1-C_4)$-alkyl and $(C_1-C_4)$-haloalkyl, or two of the radicals $R^1$ together, in the case that n is an integer greater than 1, may also be unsubstituted or substituted 1,ω-dioxoalkylene;

$R^2$ is hydrogen, $(C_1-C_6)$-alkyl, $(C_2-C_6)$-alkenyl, $(C_3-C_6)$-cycloalkyl, $(C_5-C_6)$-cycloalkenyl or substituted aryl;

$R^3$ is hydrogen, $(C_1-C_{18})$-alkyl, $(C_3-C_{12})$-cycloalkyl, $(C_2-C_{18})$-alkenyl, $(C_5-C_6)$-cycloalkenyl, $(C_2-C_8)$-alkynyl, aryl or $-N=CR^4R^5$, where each of the abovementioned carbon-containing radicals is unsubstituted or substituted by one or more identical or different radicals selected from the group consisting of halogen, nitro, cyano, hydroxyl, $(C_1-C_8)$-alkoxy where one or more $CH_2$ groups may be replaced by oxygen, $(C_1-C_8)$-alkylthio, $(C_1-C_6)$-alkylsulfinyl, $(C_1-C_6)$-alkylsulfonyl, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, mono- or di-$(C_1-C_4)$-alkylamino, $(C_1-C_8)$-alkoxycarbonyl, $(C_2-C_8)$-alkenyloxycarbonyl, $(C_2-C_8)$-alkynyloxycarbonyl, $(C_1-C_8)$-alkylthiocarbonyl, $(C_1-C_8)$-alkylcarbonyl, $(C_2-C_8)$-alkenylcarbonyl, $(C_2-C_8)$-alkynylcarbonyl, $(C_1-C_8)$-alkylcarbonylamino, $(C_2-C_8)$-alkenylcarbonylamino, $(C_2-C_8)$-alkynylcarbonylamino, $(C_1-C_8)$-alkylcarbonyloxy, $(C_1-C_8)$-alkylcarbamoyl, phenyl, phenyl-$(C_1-C_4)$-alkoxy, phenoxy, phenoxy-$(C_1-C_4)$-alkoxy and phenoxycarbonyl, where the last 28 radicals are unsubstituted or substituted by one or more identical or different radicals selected from the group consisting of halogen, nitro, amino, mono- or di-$(C_1-C_4)$-alkylamino, cyano or hydroxyl and, in the case of cyclic radicals, also of $(C_1-C_4)$-alkyl and $(C_1-C_4)$-haloalkyl and $R^4$ and $R^5$ independently of one another are each hydrogen or $(C_1-C_6)$-alkyl, or salts thereof.

2. The herbicide/safener combination as claimed in claim 1, which comprises

B) at least one compound of the formula (I) in which

X is CH;

n is an integer from 0 to 3;

$R^1$ is halogen, $(C_1-C_4)$-alkyl, $(C_2-C_4)$-alkenyl, $(C_3-C_6)$-cycloalkyl, aryl, $(C_1-C_4)$-alkoxy, $(C_2-C_4)$-alkenyloxy, $(C_2-C_4)$-alkynyloxy, phenoxy, amino, mono- or di-$(C_1-C_4)$-alkylamino, nitro, hydroxyl, mono- or di-$(C_1-C_4)$-alkylaminosulfonyl, cyano, $(C_1-C_4)$-alkylthio, $(C_1-C_4)$-alkylsulfinyl, $(C_1-C_4)$-alkylsulfonyl, $(C_1-C_4)$-alkoxycarbonyl, $(C_1-C_4)$-alkylthiocarbonyl or $(C_1-C_4)$-alkylcarbonyl, where each of the abovementioned carbon-containing radicals is unsubstituted or substituted by one or more identical or different radicals selected from the group consisting of halogen, halo-$(C_1-C_8)$-alkoxy, nitro, amino, mono- or di-$(C_1-C_4)$-alkylamino, cyano, hydroxyl and $(C_1-C_8)$-alkoxy where one or more $CH_2$ groups may be replaced by oxygen, and may also be substituted, in the case of cyclic radicals, by $(C_1-C_4)$-alkyl and $(C_1-C_4)$-haloalkyl, or two of the radicals $R^1$ together, in the case that n is an integer greater than 1, are also an unsubstituted or substituted 1,ω-dioxoalkylene;

$R^2$ is hydrogen or $(C_1-C_4)$-alkyl and $R^3$ is hydrogen, $(C_1-C_8)$-alkyl, $(C_3-C_6)$-cycloalkyl, $(C_2-C_6)$-alkenyl, $(C_2-C_6)$-alkynyl or aryl, where each of the abovementioned carbon-containing radicals is unsubstituted or substituted by one or more identical or different radicals selected from the group consisting of halogen, nitro, cyano, hydroxyl, $(C_1–C_8)$-alkoxy where one or more $CH_2$ groups may be replaced by oxygen, $(C_1–C_8)$-alkylthio, $(C_1–C_6)$-alkylsulfinyl, $(C_1–C_6)$-alkylsulfonyl, $(C_2–C_4)$-alkenyloxy, $(C_2–C_4)$-alkynyloxy, $(C_3–C_6)$-cycloalkyl, mono- or di-$(C_1–C_4)$-alkylamino, $(C_1–C_8)$-alkoxycarbonyl, $(C_1–C_4)$-alkylcarbonyl, $(C_2–C_4)$-alkenylcarbonyl, $(C_1–C_4)$-alkylcarbonyloxy, phenyl, phenyl-$(C_1–C_4)$-alkoxy, phenoxy and phenoxy-$(C_1–C_4)$-alkoxy, where the last 16 radicals are unsubstituted or substituted by one or more identical or different radicals selected from the group consisting of halogen, nitro, amino, mono- or di-$(C_1–C_4)$-alkylamino, cyano and hydroxyl and, in the case of cyclic radicals, also of $(C_1–C_4)$-alkyl and $(C_1–C_4)$-haloalkyl.

3. The herbicide/safener combination as claimed in claim 1, which comprises
B) at least one compound of the formula (I) in which
X is CH or N;
n, in the case that X=N, is an integer from 0 to 4 and, in the case that X=CH, is an integer from 0 to 5;
$R^1$ is halogen, $(C_1–C_4)$-alkyl, $(C_1–C_4)$-haloalkyl, $(C_1–C_4)$-alkoxy, $(C_1–C_4)$-haloalkoxy, nitro, $(C_1–C_4)$-alkylthio, $(C_1–C_4)$-alkylsulfonyl, $(C_1–C_4)$-alkoxycarbonyl or phenyl or phenoxy, where the last two radicals are unsubstituted or substituted by one or more, preferably up to three, identical or different radicals selected from the group consisting of halogen, $(C_1–C_4)$-alkyl, $(C_1–C_4)$-haloalkyl, $(C_1–C_8)$-alkoxy, halo-$(C_1–C_8)$-alkoxy, nitro, amino, mono- or di-$(C_1–C_4)$-alkylamino and cyano, or two of the radicals $R^1$ together, in the case that n is an integer greater than 1, are an unsubstituted or substituted 1,ω-dioxoalkylene;
$R^2$ is hydrogen or $(C_1–C_4)$-alkyl and
$R^3$ is hydrogen, $(C_1–C_8)$-alkyl, $(C_2–C_4)$-alkenyl or $(C_2–C_4)$-alkynyl, where each of the abovementioned carbon-containing radicals is unsubstituted or substituted by one or more, preferably up to three, identical or different radicals selected from the group consisting of halogen and $(C_1–C_4)$-alkoxy.

4. The herbicide/safener combination as claimed in claim 1, which comprises
A) at least one herbicidally active compound selected from the group consisting of phenoxyphenoxycarboxylic esters, heteroaryloxycarboxylic esters, sulfonylureas, cyclohexanediones, benzoylcyclohexanediones, imidazolinones, triazolopyrimidinesulfonamides, pyrimidinyloxypyrimidinecarboxylic acid derivatives, pyrimidinyloxybenzoic acid derivatives and S-(N-aryl-N-alkylcarbamoylmethyl)dithiophosphonic esters.

5. The herbicide/safener combination as claimed in claim 1, wherein the mixing ratio of component B to component A is in the range between 1:10 and 10:1.

6. A crop protection agent which comprises a herbicide/safener combination as claimed in claim 1.

7. The crop protection agent as claimed in claim 6, which comprises 0.1 to 99% by weight of a herbicide/safener combination as claimed in claim 1 in addition to formulating agents customarily used in crop protection.

8. A method for protecting crop plants against phytotoxic side effects of herbicides, which comprises applying an effective amount of at least one compound of the formula (I) before, after or together with a herbicidally active compound to plants, seeds of plants or the area under cultivation, the compound of the formula (I) or the salt thereof and the herbicide being defined as claimed in claim 1.

9. A 2-fluoracrylic acid compound of the formula (I)

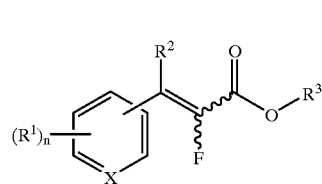

(I)

in which
X is CH or N;
n, in the case that X=N, is an integer from 0 to 4 and, in the case that X=CH, is an integer from 0 to 5;
$R^1$ is halogen, $(C_1–C_8)$-alkyl, $(C_2–C_8)$-alkenyl, $(C_2–C_8)$-alkynyl, $(C_3–C_6)$-cycloalkyl, $(C_5–C_6)$-cycloalkenyl, aryl, $(C_1–C_8)$-alkoxy, $(C_2–C_8)$-alkenyloxy, $(C_2–C_8)$-alkynyloxy, phenoxy, sulfamoyl, amino, mono- or di-$(C_1–C_4)$-alkylamino, nitro, hydroxyl, mono- or di-$(C_1–C_4)$-alkylaminosulfonyl, cyano, $(C_1–C_8)$-alkylthio, $(C_1–C_8)$-alkylsulfinyl, $(C_1–C_8)$-alkylsulfonyl, $(C_1–C_8)$-alkoxycarbonyl, $(C_1–C_8)$-alkylthiocarbonyl or $(C_1–C_8)$-alkylcarbonyl, where each of the abovementioned carbon-containing radicals is unsubstituted or substituted by one or more identical or different radicals selected from the group consisting of halogen, halo-$(C_1–C_8)$-alkoxy, phosphoryl, nitro, amino, mono- or di-$(C_1–C_4)$-alkylamino, cyano, hydroxyl and $(C_1–C_8)$-alkoxy where one or more $CH_2$ groups may be replaced by oxygen and, in the case of cyclic radicals, also of $(C_1–C_4)$-alkyl and $(C_1–C_4)$-haloalkyl, or two of the radicals $R^1$ together, in the case that n is an integer greater than 1, may also be unsubstituted or substituted 1,ω-dioxoalkylene;
$R^2$ is hydrogen, $(C_1–C_6)$-alkyl, $(C_2–C_6)$-alkenyl, $(C_3–C_6)$-cycloalkyl, $(C_5–C_6)$-cycloalkenyl or substituted aryl;
$R^3$ is hydrogen, $(C_1–C_{18})$-alkyl, $(C_3–C_{12})$-cycloalkyl, $(C_2–C_{18})$-alkenyl, $(C_5–C_6)$-cycloalkenyl, $(C_2–C_{18})$-alkynyl, aryl or —N=$CR^4R^5$, where each of the abovementioned carbon-containing radicals is unsubstituted or substituted by one or more identical or different radicals selected from the group consisting of halogen, nitro, cyano, hydroxyl, $(C_1–C_8)$-alkoxy where one or more $CH_2$ groups may be replaced by oxygen, $(C_1–C_8)$-alkylthio, $(C_1–C_6)$-alkylsulfinyl, $(C_1–C_6)$-alkylsulfonyl, $(C_2–C_8)$-alkenylthio, $(C_2–C_8)$-alkynylthio, $(C_2–C_8)$-alkenyloxy, $(C_2–C_8)$-alkynyloxy, $(C_3–C_7)$-cycloalkyl, $(C_3–C_7)$-cycloalkoxy, mono- or di-$(C_1–C_4)$-alkylamino, $(C_1–C_8)$-alkoxycarbonyl, $(C_2–C_8)$-alkenyloxycarbonyl, $(C_2–C_8)$-alkynyloxycarbonyl, $(C_1–C_8)$-alkylthiocarbonyl, $(C_1–C_8)$-alkylcarbonyl, $(C_2–C_8)$-alkenylcarbonyl, $(C_2–C_8)$-alkynylcarbonyl, $(C_1–C_8)$-alkylcarbonylamino, $(C_2–C_8)$-alkenylcarbonylamino, $(C_2–C_8)$-alkynylcarbonylamino, $(C_1–C_8)$-alkylcarbonyloxy, $(C_1–C_8)$-alkylcarbamoyl, phenyl, phenyl-$(C_1–C_4)$-alkoxy, phenoxy, phenoxy-$(C_1–C_4)$-alkoxy and phenoxycarbonyl, where the last 28 radicals are unsubstituted or substituted by one or more identical or different radicals selected from the group consisting of halogen, nitro, amino, mono- or di-$(C_1–C_4)$-alkylamino, cyano or hydroxyl and, in the case of cyclic radicals, also of $(C_1–C_4)$-alkyl and $(C_1–C_4)$-haloalkyl and
except for a) α-fluorocinnamic acid or the methyl or ethyl ester thereof,
b) ethyl 3- or 4-methyl-α-fluorocinnamate,
c) 3- or 4-chloro-α-fluorocinnamic acid or the methyl or ethyl ester thereof,
d) ethyl 2-hydroxy-α-fluorocinnamic acid,
e) ethyl α-fluoro-β-2-pyridylacrylate,
f) ethyl α-fluoro-β-3-pyridylacrylate,
g) ethyl 3- or 4-methoxy-α-fluorocinnamate,
h) ethyl 3- or 4-phenoxy-α-fluorocinnamate,
j) ethyl 4-phenyl-α-fluorocinnamate,
k) 3- or 4-fluoro-α-fluorocinnamic acid or the methyl or ethyl ester thereof,
l) 3- or 4-bromo-α-fluorocinnamic acid or the ethyl ester thereof,
m) ethyl 4-carboxyethyl-α-fluorocinnamate,
n) methyl or ethyl 3- or 4-trifluoromethyl-α-fluorocinnamate,
o) ethyl 3- or 4-cyano-α-fluorocinnamate,
p) ethyl 3- or 4-nitro-α-fluorocinnamate,
q) 3- or 4-hydroxy-α-fluorocinnamic acid,
r) α-fluoro-4-hydroxy-cinnamic acid,
s) α-fluoro-β-methyl-cinnamic acid or the ethyl ester thereof,
t) 4 amino- or 4-dimethylamino-α-fluorocinnamate,
u) t-butyl or phenyl 4-methyl-α-fluorocinnamate,
v) ethyl 3,4-dibromo-α-fluorocinnamate,
w) ethyl β-ethyl- or β-phenyl-α-fluorocinnamate.

10. A process for preparing 2-fluoroacrylic acid compound as claimed in claim 9, which comprises reacting an aldehyde or ketone of the formula (II)

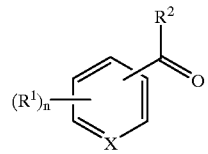

(II)

in which
  X, $R^1$, $R^2$ and n are each as defined in formula (I)
  a) with diethyloxalofluoroacetate or
  b) with triethyl 2-fluoro-2-phosphonoacetate
to give the ethyl ester which is, if $R^3$ is not ethyl, subsequently reacted by customary methods to give the compound of the formula (I).

* * * * *